US009951047B2

(12) United States Patent
Ozaki et al.

(10) Patent No.: US 9,951,047 B2
(45) Date of Patent: Apr. 24, 2018

(54) SALT OF MONOCYCLIC PYRIDINE DERIVATIVE AND CRYSTAL THEREOF

(71) Applicant: Eisai R&D Management Co., Ltd., Tokyo (JP)

(72) Inventors: Shunsuke Ozaki, Kamisu (JP); Kenshi Yoshida, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/500,429

(22) PCT Filed: Aug. 17, 2015

(86) PCT No.: PCT/JP2015/073047
§ 371 (c)(1),
(2) Date: Jan. 30, 2017

(87) PCT Pub. No.: WO2016/027781
PCT Pub. Date: Feb. 25, 2016

(65) Prior Publication Data
US 2017/0217935 A1 Aug. 3, 2017

(30) Foreign Application Priority Data

Aug. 18, 2014 (JP) .................. 2014-166118

(51) Int. Cl.
C07D 401/14 (2006.01)
A61K 31/44 (2006.01)
C07C 55/10 (2006.01)
C07C 55/02 (2006.01)

(52) U.S. Cl.
CPC ............ C07D 401/14 (2013.01); C07C 55/02 (2013.01); C07C 55/10 (2013.01); C07B 2200/13 (2013.01)

(58) Field of Classification Search
None
See application file for complete search history.

(56) References Cited

U.S. PATENT DOCUMENTS

| | | |
|---|---|---|
| 6,831,175 B2 | 12/2004 | Li et al. |
| 7,109,219 B2 | 9/2006 | Tsuruoka et al. |
| 7,253,286 B2 | 8/2007 | Funahashi et al. |
| 8,131,527 B1 | 3/2012 | Saxty et al. |
| 8,614,216 B2 | 12/2013 | Okhamafe et al. |
| 8,933,099 B2 | 1/2015 | Funasaka et al. |
| 2004/0053908 A1 | 3/2004 | Funahashi et al. |
| 2004/0122029 A1 | 6/2004 | Liu et al. |
| 2004/0204427 A1 | 10/2004 | Chen et al. |
| 2005/0187236 A1 | 8/2005 | Tsuruoka et al. |
| 2005/0256154 A1 | 11/2005 | Luk et al. |
| 2008/0108648 A1 | 5/2008 | Alcouffe et al. |
| 2011/0060215 A1 | 3/2011 | Tupin et al. |
| 2012/0270918 A1 | 10/2012 | Abecassis et al. |
| 2013/0338134 A1 | 12/2013 | Wu et al. |
| 2014/0142084 A1 | 5/2014 | Kameda et al. |
| 2014/0155385 A1 | 6/2014 | Barf et al. |
| 2014/0235614 A1* | 8/2014 | Funasaka ............ C07D 409/14 514/210.21 |
| 2015/0191791 A1 | 7/2015 | Shibata |

FOREIGN PATENT DOCUMENTS

| | | |
|---|---|---|
| CL | 201400130 | 8/2014 |
| CN | 1678607 | 10/2005 |
| EP | 1522540 | 4/2005 |
| EP | 2657233 | 8/2014 |
| JP | 2008-533111 | 3/2006 |
| JP | 2006-522756 | 10/2006 |
| JP | 2009-215313 | 9/2009 |
| JP | 5600229 | 10/2014 |
| JP | 2014-237707 | 12/2014 |
| RU | 2257380 | 7/2005 |

(Continued)

OTHER PUBLICATIONS

Cancer Genome Atlas Research Network, "Comprehensive genomic characterization of squamous cell lung cancers", Nature, 2012 vol. 489, p. 519-p. 525.
Chen et al., "Inhibition of endogenous SPARC enhances pancreatic cancer cell growth: modulation by FGFR1-III isoform expression", British Journal of Cancer, 2010 vol. 102, p. 188-p. 195.
Daniele et al., "FGF Receptor Inhibitors: Role in Cancer Therapy", Curr Oncol Rep, 2012 vol. 14, p. 111-p. 119.
French et al., "Targeting FGFR4 Inhibits Hepatocellular Carcinoma in Preclinical Mouse Models", PLoS One, 2012; vol. 7, p. 36713-1-p. 36713-12.
Gavine et al., "AZD4547:An Orally Bioavailable, Potent, and Selective Inhibitor of the Fibroblast Growth Factor Receptor Tyrosine Kinase Family", Cancer Research, 2012 vol. 72, p. 2045-p. 2056.

(Continued)

*Primary Examiner* — Zinna Northington Davis
(74) *Attorney, Agent, or Firm* — Fish & Richardson P.C.

(57) ABSTRACT

The present invention provides salts consisting of an organocarboxylic acid selected from the group consisting of succinic acid and maleic acid and a compound represented by formula (I)

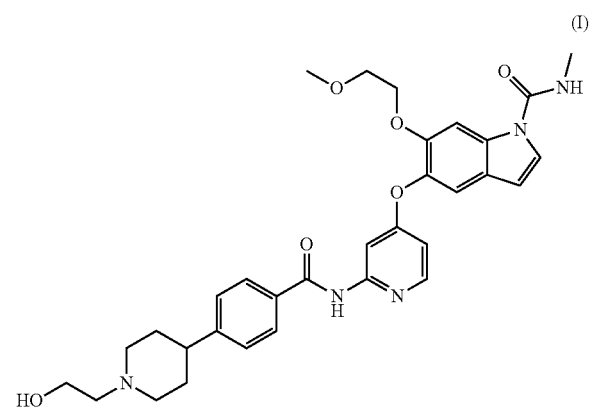

and crystals thereat which can be used as bulk materials for pharmaceuticals.

19 Claims, 15 Drawing Sheets

(56) References Cited

FOREIGN PATENT DOCUMENTS

| RU | 2310651 | 11/2007 |
|---|---|---|
| WO | 2002/032872 | 4/2002 |
| WO | 2004/020434 | 3/2004 |
| WO | 2006/000420 | 1/2006 |
| WO | WO 2006/097625 | 9/2006 |
| WO | WO 2007/071752 | 6/2007 |
| WO | WO 2008/008747 | 1/2008 |
| WO | WO 2008/012690 | 1/2008 |
| WO | 2008/075068 | 6/2008 |
| WO | WO 2008/078091 | 7/2008 |
| WO | WO 2008/078100 | 7/2008 |
| WO | WO 2009/001070 | 12/2008 |
| WO | WO 2009/019518 | 2/2009 |
| WO | WO 2009/047506 | 4/2009 |
| WO | WO 2009/047522 | 4/2009 |
| WO | WO 2009/056886 | 5/2009 |
| WO | WO 2009/076602 | 6/2009 |
| WO | WO 2009/141386 | 11/2009 |
| WO | WO 2009/150240 | 12/2009 |
| WO | WO 2009/153592 | 12/2009 |
| WO | WO 2010/078421 | 7/2010 |
| WO | WO 2010/078427 | 7/2010 |
| WO | WO 2010/078430 | 7/2010 |
| WO | WO 2010/119284 | 10/2010 |
| WO | WO 2010/119285 | 10/2010 |
| WO | WO 2011/001122 | 1/2011 |
| WO | WO 2011/001413 | 1/2011 |
| WO | WO 2011/016528 | 2/2011 |
| WO | WO 2011/051425 | 5/2011 |
| WO | WO 2011/071821 | 6/2011 |
| WO | WO 2011/135376 | 11/2011 |
| WO | WO 2012/004732 | 1/2012 |
| WO | WO 2012/073017 | 6/2012 |
| WO | WO 2012/088266 | 6/2012 |
| WO | 2013/010380 | 1/2013 |
| WO | WO 2013/061074 | 5/2013 |
| WO | WO 2013/061077 | 5/2013 |
| WO | WO 2013/061080 | 5/2013 |
| WO | WO 2013/061081 | 5/2013 |
| WO | WO 2013/087744 | 6/2013 |
| WO | WO 2013/108809 | 7/2013 |
| WO | WO 2013/129369 | 9/2013 |
| WO | WO 2013/179034 | 12/2013 |
| WO | WO 2014/007369 | 1/2014 |
| WO | WO 2014/011900 | 1/2014 |
| WO | WO 2014/026125 | 2/2014 |
| WO | WO 2014/044846 | 3/2014 |
| WO | WO 2014/048878 | 3/2014 |
| WO | WO 2014/051022 | 3/2014 |
| WO | WO 2014/129477 | 8/2014 |
| WO | WO 2014/162039 | 10/2014 |

OTHER PUBLICATIONS

Guagnano et al., "Discovery of 3-(2,6-dichloro-3,5-dimethoxyphenyl)-1-{6-[4-(4-ethyl-piperazin-1-yl)-phenylamino]-pyrimidin-4-yl}-1-methyl-urea (NVP-BGJ398), a potent and selective inhibitor of the fibroblast growth factor receptor family of receptor tyrosine kinase", Journal of Medicinal Chemistry, 2011 vol. 54, pp. 7066-7083.
International Search Report for PCT/JP2015/073047 dated Nov. 17, 2015 (English translation).
Ishiwata et al., "Enhanced Expression of Fibroblast Growth Factor Receptor 2 IIIc Promotes Human Pancreatic Cancer Cell Proliferation", The American Journal of Pathology, 2012 vol. 180, p. 1928-p. 1941.
Logie et al., "Activating mutations of the tyrosine kinase receptor FGFR3 are associated with benign skin tumors in mice and humans", Human Molecular Genetics, 2005 vol. 14, p. 1153-p. 1160.
Sasaki et al., "Increased FGFR1 copy number in lung squamous cell carcinomas", Molecular Medicine Reports, 2012 vol. 5, p. 725-p. 728.
St. Bernard et al., "Fibroblast Growth Factor Receptors as Molecular Targets in Thyroid Carcinoma", Endocrinology, 2005 vol. 146, p. 1145-p. 1153.
Tsimafeyeu et al., "Overexpression of fibroblast growth factor receptors FGFR1 and FGFR2 in renal cell carcinoma", Scandinavian Journal of Urology and Nephrology, 2011 vol. 45, p. 190-p. 195.
Turner et al., "Fibroblast growth factor signalling: from development to cancer", Nature Reviews Cancer, 2010 vol. 10, p. 116-p. 129.
Weiss et al., "Frequent and Focal FGFR1 Amplification Associates with Therapeutically Tractable FGFR1 Dependency in Squamous Cell Lung Cancer", Science Translational Medicine, 2010 vol. 2, issue 62, p. 62-p. 93.
Wesche et al., "Fibroblast growth factors and their receptors in cancer", Biochem J., 2011 vol. 437, p. 199-p. 213.
International Preliminary Report on Patentability in International Application No. PCT/JP2015/073047, dated Mar. 2, 2017, 6 pages (English Translation).
Notice of Allowance in Chinese Patent Application No. 201480009370.X, dated Jul. 25, 2017, 4 pages (English Translation).
Office Action in Singapore Patent Application No. 11201700703X, dated Jun. 8, 2017, 5 pages (English Translation).
Request to Amend Application Before Grant in Singapore Patent Application No. 11201506488W, dated Aug. 3, 2017, 21 pages (English Translation).
Submission Document in Australian Patent Application No. 2014219811, dated Aug. 22, 2017, 6 pages.
Submission Document in Singapore Patent Application No. 11201700703X, dated Jul. 19, 2017, 16 pages (English Translation).
Response in Vietnam Patent Application No. 1-2015-02994, dated Aug. 7, 2017, 2 pages (English Translation).
"Cancer classification, NCI, from internet", 2008, p. 1-p. 3.
Applicant's unpublished experimental data, 2014, 1 page.
Arai et. al, "Fibroblast Growth Factor Receptor 2 Tyrosine Kinase Fusions Define a Unique Molecular Subtype of Cholangiocarcinoma", Hepatology, 2014, vol. 59, No. 4, p. 1427-p. 1434.
Bono et al., "Inhibition of Tumor Angiogenesis and Growth by a Small-Molecule Multi-FGF Receptor Blocker with Allosteric Properties", Cancer Cell, 2013, p. 477-p. 488.
Borad et al., "Integrated Genomic Characterization Reveals Novel, Therapeutically Relevant Drug Targets in FGFR and EGFR Pathways in Sporadic Intrahepatic Cholangiocarcinoma", PLOS Genetics, 2014, vol. 10, Issue 2, p. 1-p. 21.
Bucci et al., "Circadian Rhythms: channels contribute," Nature Chem Bio., Jun. 2013, 9:349.
Celina Ang, "Role of the fibroblast growth factor receptor axis incholangiocarcinoma", Journal of Gastroenterology and Hepatology, 2015, vol. 30, p. 1116-p. 1122.
European Search Report in European Application No. 14754294.8, dated Jul. 15, 2016, 5 pages.
Guagnano et al., "FGFR Genetic Alterations Predict for Sensitivity to NVP-BGJ398, a Selective Pan-FGFR Inhibitor", Cancer Discovery, Sep. 20, 2012, p. 1118-p. 1133.
Harbinski et al., "Rescue Screens with Secreted Proteins Reveal Compensatory Potential of Receptor Tyrosine Kinases in Driving Cancer Growth", Cancer Discovery, Aug. 8, 2012, p. 948-p. 958.
International Preliminary Report on Patentability in International Application No. PCT/JP2014/053819, dated Sep. 3, 2015, 7 pages.
International Preliminary Report on Patentability in Patent Application No. PCT/JP2016/059162, dated Oct. 5, 2017, 8 pages (English Translation).
International Search Report in International Application No. PCT/JP2014/053819, dated Apr. 15, 2014, 9 pages.
International Search Report in International Application No. PCT/JP2016/059162, dated May 24, 2016, 2 pages (English Translation).
Li et al., "Preparation of heteroaryls for therapeutic use in pharmaceutical compositions as kinase inhibitors for treatment of hyperproliferative diseases, including cancer," 2003, CA139:323437.

(56) References Cited

OTHER PUBLICATIONS

Mohammadi et al., "Crystal structure of an angiogenesis inhibitor bound to the FGF receptor tyrosine kinase domain", The EMBO Journal vol. 17 No. 20, 1998, p. 5896-p. 5904.
Nicholas et al., "Fibroblast growth factor signaling: from development to cancer", Nature Reviews Cancer, 2010(10), p. 116-p. 129.
Norman et al., "Protein-Ligand Crystal Structures Can Guide the Design of Selective Inhibitors of the FGFR Tyrosine Kinase", Journal of Medicinal Chemistry, May 21, 2012, p. 5003-p. 5012.
Notice of Allowance in Australian Patent Application No. 2014219811, dated Sep. 13, 2017, 3 pages.
Notice of Allowance in European Patent Application No. 14754294.8, dated Jan. 4, 2017, 239 pages.
Notice of Allowance in European Patent Application No. 14754294.8, dated Mar. 9, 2017, 2 pages.
Notice of Allowance in Japanese Patent Application No. P2015-560425, dated Apr. 19, 2016, 6 pages (English Translation).
Notice of Allowance in Singapore Patent Application No. 11201506488W, dated Sep. 20, 2017 (English Translation).
Notice of Allowance in Singapore Patent Application No. 11201700703X, dated Sep. 12, 2017, 5 pages (English Translation).
Notice of Allowance in South African Application No. 2015/05941, dated May 24, 2016, 6 pages.
Notice of Allowance in U.S. Appl. No. 14/183,864, dated Nov. 19, 2014, 11 pages.
Office Action in Chinese Application No. 201480009370.X, dated Jan. 9, 2017, 10 pages (English Translation).
Office Action in Chinese Application No. 201480009370.X, dated May 26, 2016, 7 pages (English Translation).
Office Action in Israeli Application No. 240623, dated Jan. 19, 2016, 5 pages (English Translation).
Office Action in Japanese Application No. P2015-560425, dated Mar. 8, 2016, 4 pages (English Translation).
Office Action in Pakistan Application No. 94/2014, dated May 13, 2016, 2 pages.
Office Action in Russian Patent Application No. 2015134558, dated Aug. 24, 2017, 11 pages (English Translation).
Office Action in U.S. Appl. No. 14/183,864, dated Jun. 4, 2014, 7 pages.
Office Action in U.S. Appl. No. 14/183,864, dated Sep. 16, 2014.
Office Action in Ukraine Patent Application No. a201508149, dated Aug. 11, 2017, 6 pages (English Translation).
Patani and LaVoie, "Bioisosterism: A Rational Approach in Drug Design," Chem. Rev., 1996, 96:3147-3176.
Response in Gulf Cooperation Council Patent Application No. GCC/P/2014/26467, dated Aug. 27, 2017, 18 pages (English Translation).
Rubini et al., "Synthesis of Isosteric Methylene-Oxy Pseudodipeptide Analogues as Novel Amide Bond Surrogate Units", Tetrahedron, vol. 42, No. 21, 1986, p. 6039-p. 6045.
Shibata, "Clinical significance of Expression oFGFR2 Fusion Genes in Bile Duct Cancer", The Bilialy Tract & Pancreas, Feb. 12, 2015, vol. 36(2), p. 137-p. 142.
Submission Document in Argentine Patent Application No. P140100495, dated Jan. 23, 2015, 7 pages (English Translation).
Submission Document in Brazil Patent Application No. BR112015019790-6, dated Apr. 28, 2016, 19 pages (English Translation).
Submission Document in Brazil Patent Application No. BR112015019790-6, dated Dec. 22, 2015, 12 pages (English Translation).
Submission Document in Chilean Patent Application No. 2015-02311, dated Jan. 8, 2016, 8 pages.
Submission Document in Chilean Patent Application No. 2015-02311, dated Jun. 13, 2017, 38 pages (English Translation).
Submission Document in Chinese Patent Application No. 201480009370.X, dated Feb. 25, 2016, 18 pages (English Translation).
Submission Document in Chinese Patent Application No. 201480009370.X, dated Mar. 21, 2017, 41 pages (English Translation).
Submission Document in Chinese Patent Application No. 201480009370.X, dated Oct. 10, 2016, 59 pages (English Translation).
Submission Document in Egypt Patent Application No. PCT1285/2015, dated Aug. 19, 2015, 2 pages (English Translation).
Submission Document in European Patent Application No. 14754294.8, dated Nov. 10, 2016, 9 pages.
Submission Document in Indian Patent Application No. 4989/CHENP/2015, dated May 9, 2016, 7 pages (English Translation).
Submission Document in Indonesia Patent Application No. P-00201505035, dated Apr. 27, 2016, 10 pages (English Translation).
Submission Document in Indonesia Patent Application No. P-00201505035, dated Dec. 5, 2016, 3 pages.
Submission Document in Israeli Patent Application No. 240623, dated May 18, 2016, 3 pages (English Translation).
Submission Document in Japanese Patent Application No. 2014-526292, dated May 30, 2014, 14 pages (English Translation).
Submission Document in Japanese Patent Application No. P2015-560425, dated Mar. 24, 2016, 8 pages (English Translation).
Submission Document in Malaysian Patent Application No. PI 2015702696, dated Apr. 7, 2016, 4 pages.
Submission Document in Malaysian Patent Application No. PI 2015702696, dated Jan. 6, 2016, 207 pages.
Submission Document in New Zealand Patent Application No. 711101, dated Apr. 12, 2016, 9 pages.
Submission Document in New Zealand Patent Application No. 711101, dated Jan. 20, 2016, 5 pages.
Submission Document in Pakistan Patent Application No. 94/2014, dated Aug. 25, 2016, 14 pages.
Submission Document in Peru Patent Application No. 001748-2015, dated Dec. 21, 2015, 9 pages (English Translation).
Submission Document in Philippines Patent Application No. 1-2015-501813, dated Apr. 4, 2016, 1 page (English Translation).
Submission Document in Philippines Patent Application No. 1-2015-501813, dated Dec. 21, 2015, 3 pages (English Translation).
Submission Document in Russian Patent Application No. 2015134558, dated Apr. 22, 2016, 14 pages (English Translation).
Submission Document in Russian Patent Application No. 2015134558, dated Dec. 25, 2015, 16 pages.
Submission Document in Singapore Patent Application No. 11201506488W, dated Dec. 23, 2015, 5 pages.
Submission Document in Ukraine Patent Application No. a201508149, dated Oct. 6, 2015, 4 pages (English Translation).
Submission Document in Vietnam Patent Application No. 1-2015-02994, dated May 25, 2016, 12 pages (English Translation).
Submission Document in Vietnam Patent Application No. 1-2015-02994, dated Oct. 28, 2015, 22 pages (English Translation).
Zhang et al., "Translating the Therapeutic Potential of AZD4547 in FGFR1-Amplified Non-Small Cell Lung Cancer through the Use of Patient-Derived Tumor Xenograft Models", Clinical Cancer Research, May 24, 2013, p. 6657-p. 6667.
Notice of Allowance in Vietnam Patent Application No. 1-2015-02994, dated Oct. 23, 2017, 2 pages (English Translation).
Office Action in Australian Patent Application No. 2014219811, dated Jun. 16, 2017, 2 pages.
Office Action in Chilean Patent Application No. 2015-02311, dated Mar. 22, 2017, 21 pages (English Translation).
Office Action in Gulf Cooperation Council Patent Application No. GCC/P/2014/26467, dated Jun. 7, 2017, 7 pages (English Translation).
Office Action in Russian Patent Application No. 2015134558, dated Oct. 21, 2015, 3 pages (English Translation).
Office Action in Thai Patent Application No. 1501004679, dated Sep. 26, 2017, 4 pages (English Translation).
Office Action in Ukraine Patent Application No. a201508149, dated Oct. 6, 2015, 2 pages (English Translation).
Office Action in Vietnam Patent Application No. 1-2015-02994, dated Jun. 21, 2017, 2 pages (English Translation).
Office Action in Vietnam Patent Application No. 1-2015-02994, dated Sep. 30, 2015, 4 pages (English Translation).

\* cited by examiner

SALT OF MONOCYCLIC PYRIDINE DERIVATIVE AND CRYSTAL THEREOF

TECHNICAL FIELD

The present invention relates to a salt of a monocycle pyridine derivative and a crystal thereof having an FGFR inhibitory action.

BACKGROUND ART

An FGF (fibroblast growth factor) is known as a growth factor for controlling a variety of physiological functions such as cell growth, cell migration, cellular infiltration, cell survival, differential induction, wound healing and angiogenesis.

The FGF controls the various physiological functions via FGF receptors (FGFRs: FGFR1, FGFR2, FGFR3 and FGFR4), that is, receptor tyrosine kinases. Each FGFR includes three types of domains of an extracellular domain, a transmembrane domain and an intracellular tyrosine kinase domain. When an FGF binds to the extracellular domain of an FGFR, a dimer of the receptor is formed. Thereafter, the intracellular tyrosine kinase is activated, and then, an intracellular signal is transmitted mainly via a MAPK (mitogen-activated protein kinase)/ERK (extracellular signal-regulated kinase) pathway or a PI3K (phosphatidylinositol 3-kinase)/Akt pathway.

Meanwhile, it has been reported that various cancers such as breast cancer, bladder cancer, EMS (8p11 myeloproliferative syndrome), stomach cancer, endometrial cancer and prostatic cancer are caused as a result of induction of FGF/FGFR signal abnormality accompanying FGF production enhancement, FGFR gene amplification, FGFR overexpression, FGFR fusion protein production, FGFR mutation and the like (Non Patent Literature 1). Furthermore, the following have been reported as cancers accompanied by the FGF/FGFR signal abnormality: Non-small-cell lung carcinoma, small-cell lung carcinoma, ovarian cancer, sarcoma, colon cancer, melanoma, glioblastoma, astrocytoma, and head and neck cancer (Non Patent Literatures 2 and 3), thyroid cancer (Non Patent Literature 4), pancreatic cancer (Non Patent Literatures 5 and 6), liver cancer (Non Patent Literature 7), skin cancer (Non Patent Literature 8), kidney cancer (Non Patent Literature 9), and lung squamous cell carcinoma and the like (Non Patent Literatures 10, 11, and 12).

Besides, the FGF/FGFR signal is one of main angiogenic signals in endothelial cells along with a VEGF (vascular endothelial growth factor)/KDR (kinase-insert domain-containing receptor) signal, and is reported to be involved in the interaction between cancer stromal cells (fibroblasts) and cancer cells (Non Patent Literature 1).

Accordingly, an FGFR inhibitor targeting an FGF/FGFR signal is expected to work as an antitumor drug, against cancers accompanied by the FGF/FGFR signal abnormality, based on its inhibitory action against the signal abnormality and its inhibitory action against the angiogenic signal. Recently, a selective FGFR inhibitor regarded to be insusceptible to be affected by a confronting effect of another signal, such as a selective FGFR inhibitor against FGFR1, FGFR2 or FGFR3, which is obviously different in the structure from a compound of the present invention, has been reported. In the development as an antitumor drug for humans, however, the selective FGFR inhibitor falls behind an antitumor drug simultaneously targeting both the FGF/FGFR signal and the VEGF/KDR signal, and has not been put on the market yet (Non Patent Literatures 13 and 14; Patent Literatures 1 and 2). Patent Literature 3 discloses pyrimidine derivatives but does not disclose an inhibitory action against the signal abnormality of the FGF/FGFR signal. Patent Literature 4 discloses pyridine derivatives or pyrimidine derivatives that inhibit angiogenesis induced by the VEGF and the FGF. None of these literatures, however, discloses the compounds of the present invention.

CITATION LIST

Patent Literature

Patent Literature 1: International Publication No. WO 2008/075068
Patent Literature 2: International Publication No. WO 2006/000420
Patent Literature 3: International Publication No. WO 2002/032872
Patent Literature 4: International Publication No. WO 2004/020434

Non Patent Literature

Non Patent Literature 1: Nicholas et at, "Fibroblast growth factor signalling: from development to cancer", Nature Reviews Cancer. 2010; 10: 116-129
Non Patent Literature 2: Jorgen WESCHE et al., Fibroblast growth factors and their receptors in cancer, Biochem J. 2011: 437; 199-213
Non Patent Literature 3: Gennaro Daniele et al., FGF Receptor Inhibitors: Role in Cancer Therapy, Curr Oncol Rep. 2012; 14:111-119
Non Patent Literature 4: Rosanne St. Bernard et at, Fibroblast Growth Factor Receptors as Molecular Targets in Thyroid Carcinoma, Endocrinology. 2005; 146: 1145-1153
Non Patent Literature 5: Toshiyuki Ishiwata et al., Enhanced Expression of Fibroblast Growth Factor Receptor 2 IIIc Promotes Human Pancreatic Cancer Cell Proliferation, Am J Pathol. 2012; 180: 1928-1941
Non Patent Literature 6: G Chen et al., Inhibition of endogenous SPARC enhances pancreatic cancer cell growth: modulation by FGFR1-III isoform expression, Br J Cancer. 2010; 102: 188-195
Non Patent Literature 7: Dorothy M. French et al., Targeting FGFR4 Inhibits Hepatocellular Carcinoma in Preclinical Mouse Models, PLoS One. 2012; 7: e36713
Non Patent Literature 8: Armelle Logie et al., Activating mutations of the tyrosine kinase receptor FGFR3 are associated with benign skin tumors in mice and humans, Hum Mol Genet 2005; 14: 1153-1160
Non Patent Literature 9: Tsimafeyeu I et al., Overexpression of fibroblast growth factor receptors FGFR1 and FGFR2 in renal cell carcinoma, Scand J Urol Nephrol 2011; 45: 190-195
Non Patent Literature 10: Jonathan Weiss et al., Frequent and Focal FGFR1 Amplification Associates with Therapeutically Tractable FGFR1 Dependency in Squamous Cell Lung Cancer, Sci Transl Med. 2010; 2: issue 62 62-93
Non Patent Literature 11: Hidefurni Sasaki et al., Increased FGFR1 copy number in lung squamous cell carcinomas, Mol Med Report. 2012; 5: 725-728
Non Patent Literature 12: The Cancer Genome Atlas Research Network, Comprehensive genomic characterization of squamous cell lung cancers, Nature 2012; 489: 519-525

Non Patent Literature 13: Paul R Lavine et al., AZD4547: An Orally Bioavailable, Potent, and Selective Inhibitor of the Fibroblast Growth Factor Receptor Tyrosine Kinase Family, Cancer Res. 2012; 72: 2045-2056

Non Patent Literature 14: Vito Guagnano et al., Discovery of 3-(2,6-Dichloro-3,5-dimethoxy-phenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase, J Med Chem. 2011; 54: 7066-7083

SUMMARY OF INVENTION

Technical Problem

A compound represented by the following formula (I) 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide, hereinafter referred to as the compound (I)) has FGFR1, FGFR2 and FGFR3 inhibitory actions. Generally, the physical properties of a compound, a salt thereof, and their crystals used as a pharmaceutical product largely influence on the bioavailability of a drug, the purity of an active pharmaceutical ingredient, prescription of a preparation and the like. An object of the present invention is therefore to provide a salt of compound (I) or a crystal thereof, which can be used as bulk materials for pharmaceuticals.

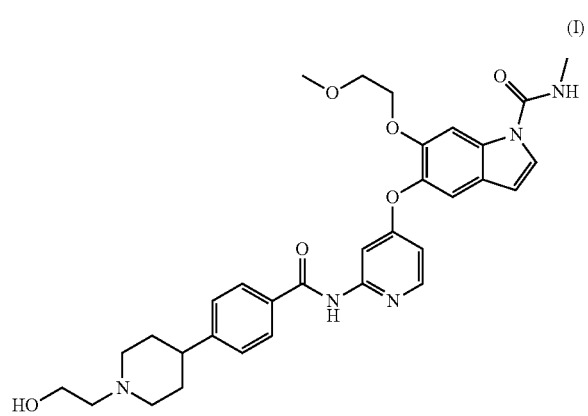 [SMILES: CNC(=O)n1ccc2cc(Oc3ccnc(NC(=O)c4ccc(C5CCN(CCO)CC5)cc4)c3)c(OCCOC)cc21]

(I)

The present inventors have made earnest studies of compound (I) in consideration of the aforementioned circumstances, and as a result, have found salts of compound (I) or crystals thereof, thereby completing the invention.

Solution to Problem

Specifically, the present invention provides the following [1] to [17].

[1] A salt consisting of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide represented by formula (I):

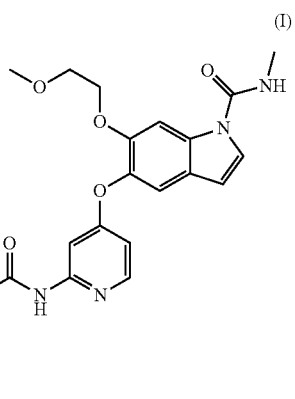

(I)

and succinic acid or maleic acid.

[2] The salt according to [1] above, which is a succinate salt.

[3] The salt according to [1] above, which is a maleate salt.

[4] The salt according to [2] above, which is 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 1.5 succinate salt.

[5] The salt according to [2] above, which is 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 0.5 succinate salt.

[6] The salt according to [1] above, which is 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide maleate salt.

[7] A crystal of a salt consisting of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide represented by formula (I):

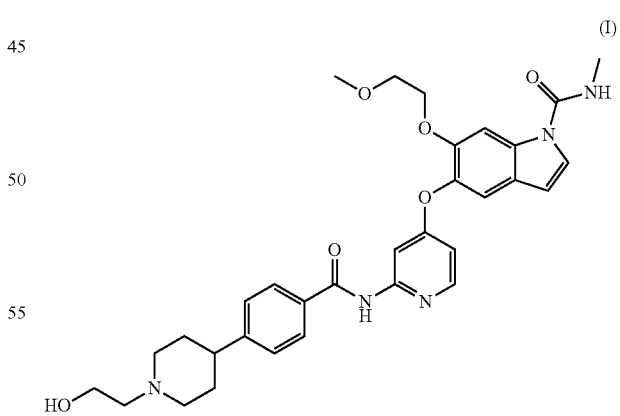

(I)

and succinic acid or maleic acid.

[8] A crystal of a salt consisting of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide represented by formula (I):

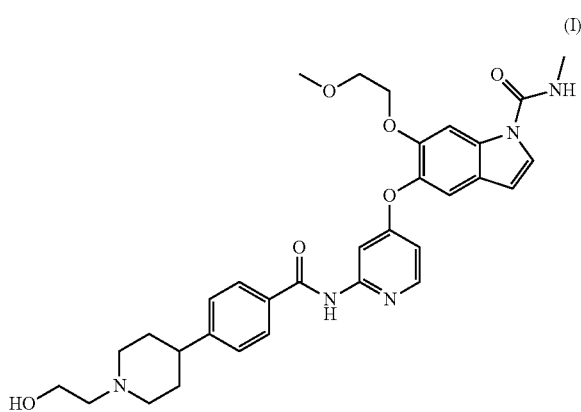 [SMILES: CNC(=O)n1ccc2cc(Oc3ccnc(NC(=O)c4ccc(C5CCN(CCO)CC5)cc4)c3)c(OCCOC)cc21]

and succinic acid.

[9] A crystal of a salt consisting of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide represented by formula (I):

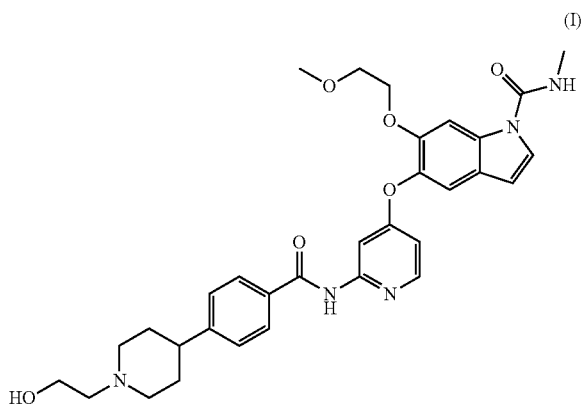 [SMILES: CNC(=O)n1ccc2cc(Oc3ccnc(NC(=O)c4ccc(C5CCN(CCO)CC5)cc4)c3)c(OCCOC)cc21]

and maleic acid.

[10] A crystal of 5-({2-[({4-[1-(2-hydroxyethydroxyethyl)piperidin-4-yl]phenyl}carbonyl)amino]pyridin-4-yl}oxy)-6-(2-methoxyethoxy)-N-methyl-1H-indole-1-carboxamide 1.5 succinate salt, having a diffraction peak at a diffraction angle (2θ±0.2°) of 22.4° in a powder X-ray diffraction.

[11] The crystal according to [10] above, having diffraction peaks at diffraction angles (2θ±0.2°) of 22.4°, 25.3° and 23.3° in a powder X-ray diffraction.

[12] A crystal (α) of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 0.5 succinate salt, having a diffraction peak at diffraction angles (2θ±0.2°) of 19.8° in a powder X-ray diffraction.

[13] A crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide maleate salt, having a diffraction peak at a diffraction angle (2θ±0.2°) of 20.1° in a powder X-ray diffraction.

[14] A crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide succinate salt, having peaks at chemical shifts (±0.5 ppm) of 108.5 ppm, 155.1 ppm and 179.9 ppm in a $^{13}C$ solid state NMR spectrum.

[15] The crystal according to [14] above, having peaks at chemical shifts (±0.5 ppm) of 27.1 ppm, 34.8 ppm, 108.5 ppm, 155.1 ppm and 179.9 ppm in a $^{13}C$ solid state NMR spectrum.

[16] A crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 1.5 succinate salt, having a powder X-ray diffraction pattern as shown in FIG. 1.

[17] A pharmaceutical composition comprising the salt or crystal according to [1]-[16] above as an active ingredient.

Advantageous Effects of Invention

The salts of compound (I) and the crystals thereof provided by the present invention possess properties as shown in the examples, hygroscopicity as shown in test examples described in later and a potential to be used as drug substance in pharmaceuticals.

DESCRIPTION OF EMBODIMENTS

Figure 1:
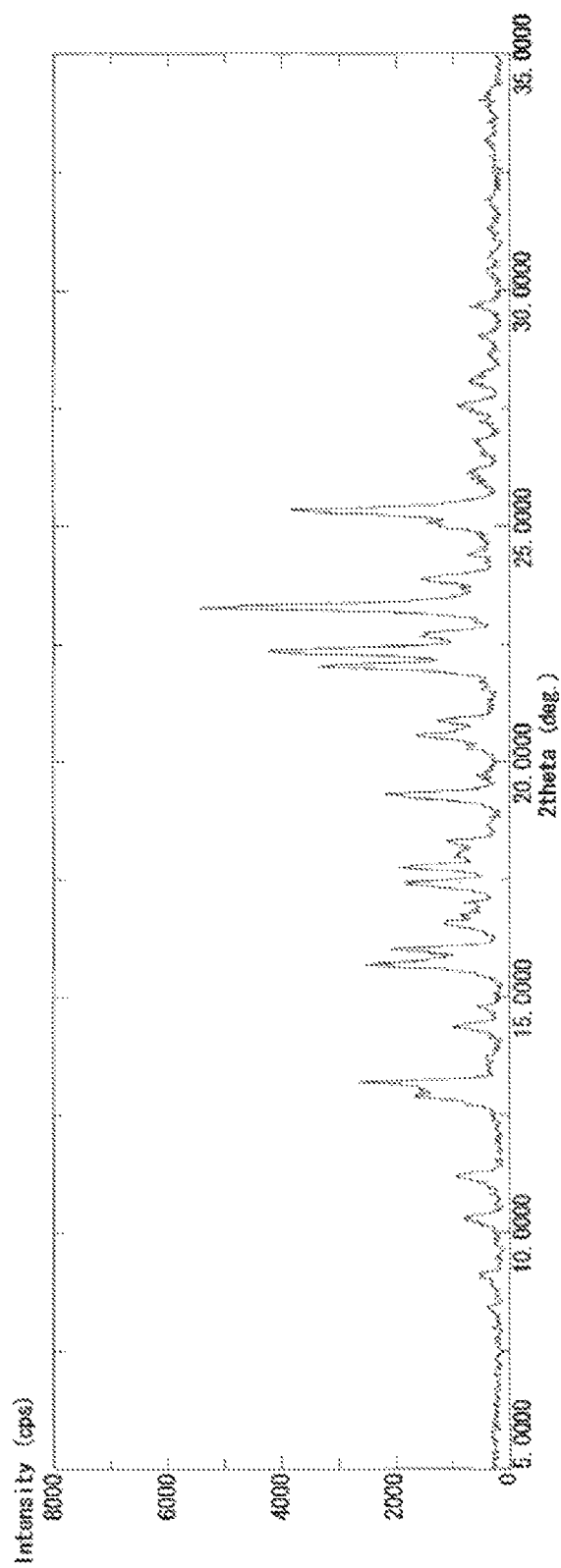
FIG. 1 is a powder X-ray diffraction pattern of the crystal of the compound (I) 1.5 succinate salt obtained in Example 1. The abscissa shows the diffraction angle (2θ) and the ordinate shows the peak intensity.
Figure 2:
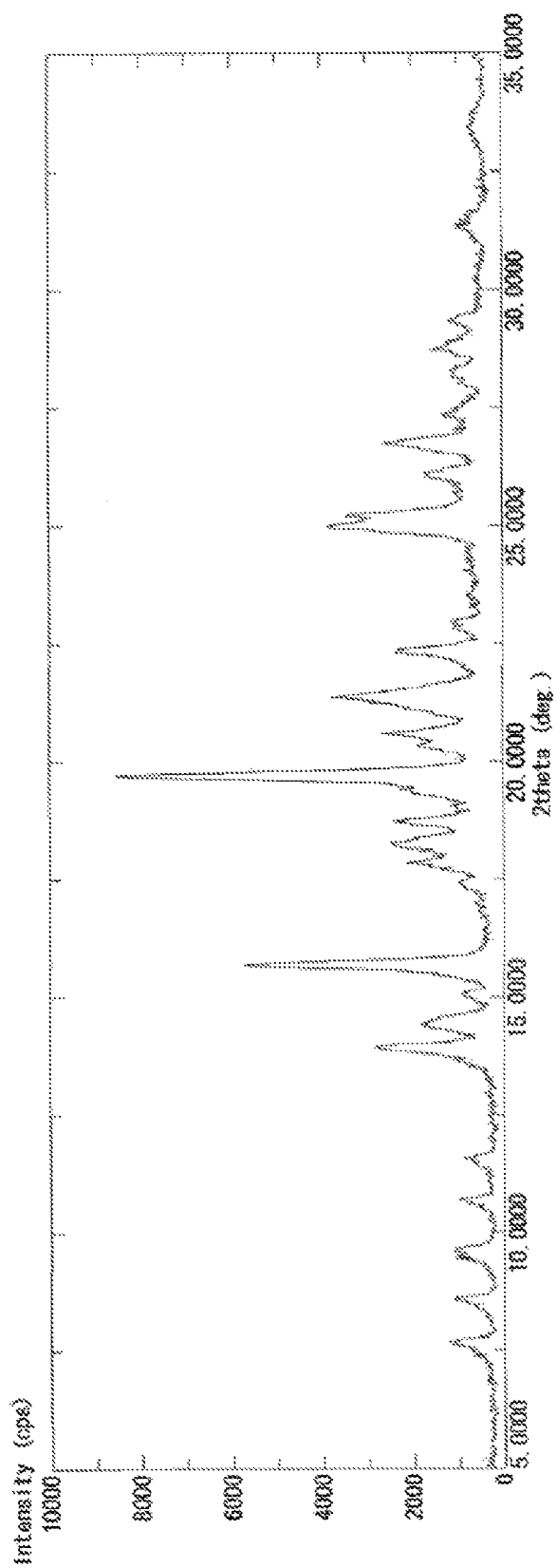
FIG. 2 is a powder X-ray diffraction pattern of the crystal of the compound (I) 0.5 succinate salt (α) obtained in Example 2. The abscissa shows the diffraction angle (2θ) and the ordinate shows the peak intensity.
Figure 3:
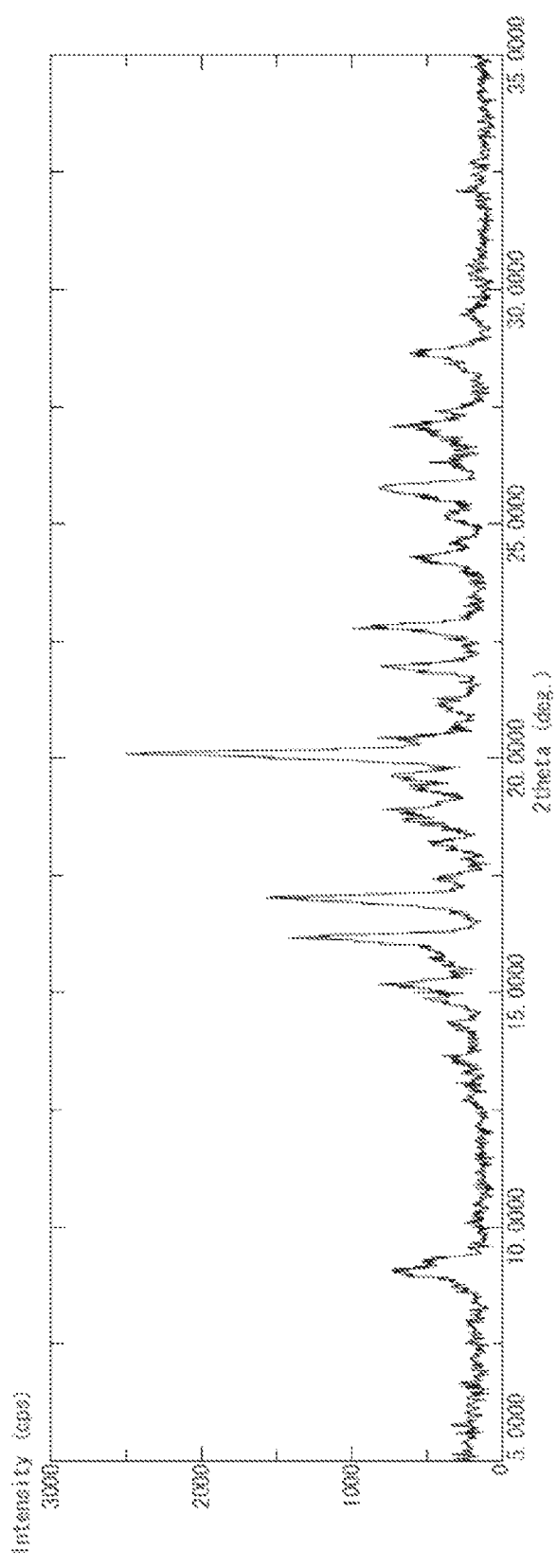
FIG. 3 is a powder X-ray diffraction pattern of the crystal of the compound (I) maleate salt obtained in Example 3. The abscissa shows the diffraction angle (2θ) and the ordinate shows the peak intensity.

A salt of the compound (I) of the present invention, a crystal thereof, and production methods thereof will be described in detail below.

In the present description, a "salt" refers to a chemical entity made up of the compound (I) as the basic component and a specific number of equivalents of an acid to the compound (I).

Examples of a "salt" used herein include salts with inorganic acids, salts with organic acids, and salts with acidic amino acids, and in particular, pharmaceutically acceptable salts are preferred.

Preferable examples of a salt with an inorganic acid include salts with hydrochloric acid, hydrobromic acid, sulfuric acid, nitric acid, phosphoric acid and the like, and preferable examples of a salt with an organic acid include salts with organic carboxylic acids such as acetic acid, succinic acid, fumaric acid, maleic acid, tartaric acid, malic acid, citric acid, lactic acid, stearic acid and benzoic acid and salts with organic sulfonic acids such as methanesulfonic acid (mesyl acid), ethanesulfonic acid, benzenesulfonic acid and p-toluenesulfonic acid (tosyl acid); in particular, succinic acid and maleic acid are preferred and succinic acid is especially preferred.

Preferable examples of a salt with an acidic amino acid include salts with aspartic acid and glutamic acid and the like.

Salts according to the present invention may be anhydrous, hydrate or solvate. As used herein, a hydrate or a solvate refers to a solid that the compound (I) or salt thereof and water molecules or solvent molecules together form, and the solid may be a crystalline. Examples of solvents in the solvates include ketone solvents such as acetone, 2-butanone and cyclohexanone; ester solvents such as methyl acetate and ethyl acetate; ether solvents such as 1,2-dimethoxyethane and t-butyl methyl ether; alcohol solvents such as methanol, ethanol, 1-propanol and isopropanol; and polar solvents such as N-methyl-2-pyrrolidone, N,N-dimethylformamide and dimethylsulfoxide. The number of water molecules or solvent molecules with respect to the compound (I) or salt thereof is not particularly limited, and examples thereof include one molecule or two molecules.

As used herein, a "crystal" refers to a crystal of a compound (I) or a salt thereof. Accordingly, a crystal of compound (I) 1.5 succinate salt, for example, means a crystal of a salt formed between compound (I) and succinic acid, having 1.5 molecules of succinic acid for 1 molecule of the compound (I).

Examples of crystals preferred herein include a crystal of a compound (i) 1.5 succinate salt, having a diffraction peak at a diffraction angle (2θ±0.2°) of 22.4° in powder X-ray diffraction;

a crystal of a compound (I) 1.5 succinate salt, having diffraction peaks at diffraction angles (2θ±0.2°) of 22.4° and 25.3° in powder X-ray diffraction;

a crystal of a compound (I) 1.5 succinate salt, having diffraction peaks at diffraction angles (2θ±0.20) of 22.4°, 25.3° and 23.3° in powder X-ray diffraction;

a crystal of a compound (I) 1.5 succinate salt, having diffraction peaks at diffraction angles (2θ±0.2°) of 22.4°, 25.3°, 23.3°, 13.2° and 22.0° in powder X-ray diffraction;

a crystal of a compound (I) 1.5 succinate salt, having diffraction peaks at diffraction angles (2θ±0.2°) of 22.4°, 25.3°, 23.3°, 13.2°, 22.0°, 19.3°, 15.7°, 22.70, 20.6° and 16.0° in powder X-ray diffraction;

a crystal of a compound (I) 0.5 succinate salt (α), having diffraction peak at diffraction angle (2θ±0.2°) of 19.8° in powder X-ray diffraction;

a crystal of a compound (I) 0.5 succinate salt (α), having diffraction peaks at diffraction angles (2θ±0.2°) of 19.8° and 15.7° in powder X-ray diffraction;

a crystal of a compound (I) 0.5 succinate salt (α), having diffraction peaks at diffraction angles (2θ±0.2°) of 19.8°, 15.7° and 13.9° in powder X-ray diffraction;

a crystal of a compound (I) 0.5 succinate salt (α), having diffraction peaks at diffraction angles (2θ±0.2°) of 19.8°, 15.70, 13.9°, 21.4° and 25.0° in powder X-ray diffraction;

a crystal of a compound (I) 0.5 succinate salt (α), having diffraction peaks at diffraction angles (2θ±0.2°) of 19.8°, 15.7°, 13.9°, 21.4°, 25.00, 20.6°, 18.2°, 26.80, 18.8° and 22.4° in powder X-ray diffraction;

a crystal of a compound (I) 0.5 succinate salt (β), having diffraction peak at diffraction angle (2θ±0.2°) of 16.6° in powder X-ray diffraction;

a crystal of a compound (I) 0.5 succinate salt (β), having diffraction peaks at diffraction angles (2θ±0.2°) of 16.6° and 19.70 in powder X-ray diffraction;

a crystal of a compound (I) 0.5 succinate salt (β), having diffraction peaks at diffraction angles (2θ±0.2°) of 16.60, 19.7° and 15.7° in powder X-ray diffraction;

a crystal of a compound (I) 0.5 succinate salt (β), having diffraction peaks at diffraction angles (2θ±0.2°) of 16.6°, 19.70, 15.7°, 9.3° and 14.3° in powder X-ray diffraction;

a crystal of a compound (I) 0.5 succinate salt (3), having diffraction peaks at diffraction angles (2θ±0.2°) of 16.6°, 19.70, 15.70, 9.30, 14.30, 21.80, 20.60, 18.7°, 18.10 and 26.50 in powder X-ray diffraction;

a crystal of a compound (I) maleate salt, having diffraction peak at diffraction angle (2θ±0.2°) of 20.1 in powder X-ray diffraction;

a crystal of a compound (I) maleate salt, having diffraction peaks at diffraction angles (2θ±0.2°) of 20.1° and 17.0° in powder X-ray diffraction;

a crystal of a compound (I) maleate salt, having diffraction peaks at diffraction angles (2θ±0.2°) of 20.10, 17.0° and 16.2° in powder X-ray diffraction;

a crystal of a compound (I) maleate salt, having diffraction peaks at diffraction angles (2θ±0.20) of 20.1°, 17.0°, 16.2°, 22.8° and 21.9° in powder X-ray diffraction;

a crystal of a compound (I) maleate salt, having diffraction peaks at diffraction angles (2θ±0.2°) of 20.1°, 17.0°, 16.20, 22.8°, 21.9°, 25.8°, 9.0°, 15.2°, 24.3° and 19.6° in powder X-ray diffraction;

a crystal of a compound (I) 1.5 succinate salt, characterized by having peaks at chemical shifts (±0.5 ppm) of 108.5 ppm, 155.1 ppm and 179.9 ppm in a $^{13}$C solid-state NMR spectrum; or a crystal of a compound (I) 1.5 succinate salt, characterized by having peaks at chemical shifts (±0.5 ppm) of 27.1 ppm, 34.8 ppm, 108.5 ppm, 155.1 ppm and 179.9 ppm in a $^{13}$C solid-state NMR spectrum.

The peaks in powder X-ray diffraction, described above, are characteristic of the respective crystals and characteristic diffraction peaks of the crystals of the compound (I) 1.5 succinate salts, the compound (I) 0.5 succinate salts (α) and (β), the compound (I) maleate salts.

Generally, errors in diffraction angles (2θ) within the range of ±0.20 may arise in powder X-ray diffraction, and thus the above-described values of diffraction angles need to be considered to include values within the range of approximately ±0.2°. Included in the present invention are, therefore, not only crystals of certain salts with peaks at exactly the same diffraction angles in powder X-ray diffraction, but also crystals with peaks within an error range of approximately ±0.20 of the diffraction angles.

Hence, "having a diffraction peak at a diffraction angle (2θ±0.2°) of 22.40" as used herein, for example, means "having a diffraction peak at a diffraction angle (2θ) of 22.2° to 22.6°". The same is also applied to other diffraction angles.

Generally, peak intensities and half-value widths of diffraction angles (2θ) in powder X-ray diffraction are different for each measurement because of differences in measurement conditions and dispersions of size and shape of each particle of powder crystal and not always stable even though forms of crystals are same. Therefore, in case of comparing a powder X-ray diffraction pattern, when diffraction angles (2θ) are the same but peak intensities and half-value widths are different those differences does not imply they are derived from differences in crystal form. Thus, a crystal of salt having a powder X-ray diffraction pattern, which has aforementioned differences with respect to characteristic diffraction peaks of a certain crystal of salt according to the present invention, means that the crystal has the same crystal form of the crystal of salt according to the present invention. As used herein, "having a powder X-ray diffraction pattern according to FIG. 1." means it includes not only the case of having exactly the same pattern as shown in FIG. 1, but also the case of having the same characteristic diffraction angles but peak intensities and half-value widths are different. Thus every crystal having such the powder X-ray diffraction pattern means that the crystal is identical to the crystal according to the present invention.

As used herein, "having peaks at chemical shifts (±0.5 ppm) of 27.1 ppm, 34.8 ppm, 108.5 ppm, 155.1 ppm and 179.9 ppm" means "having peaks each substantially equivalent to the peaks at chemical shifts (±0.05 ppm) of 27.1 ppm, 34.8 ppm, 108.5 ppm, 155.1 ppm and 179.9 ppm, when $^{13}$C solid-state NMR spectrometry is performed under a conventional measurement condition or substantially the same condition as in the present specification".

When determining whether "having peaks substantially equivalent to" or not, the above-described values of the chemical shifts need to be considered to include values within the range of approximately ±0.5 ppm since generally errors in chemical shifts (ppm) within the range of ±0.5 ppm may arise in a $^{13}$C solid-state NMR spectrum. Included in the present invention are, therefore, not only crystals with exactly the same chemical shifts in a $^{13}$C solid-state NMR spectrum, but also crystals with chemical shifts within an error range of approximately ±0.5 ppm. Hence, "having a peak at chemical shift (±0.5 ppm) of 27.1 ppm" as used herein, for example, means "having a peak at a chemical shift of 26.6 ppm to 27.6 ppm". The same is also applied to other chemical shifts in $^{13}$C solid-state NMR spectra.

The method for producing salts of compound (I) or crystals thereof or the like, which are one embodiment according to the present invention, will be illustrated below.

Production of Compound (I)

Compound (I) can be synthesized as described specifically in Production Example 1 below.

Methods for Producing Salts of Compound (I)

Salts of compound (I) according to the present invention can be obtained by conventional methods for producing salts. Specifically, they can be produced, for example, by suspending or dissolving compound (I) in a solvent, with heating if necessary, then by adding to the obtained suspension or solution an acid, and by stirring or leaving the resultant suspension or solution for several minutes to several days at room temperature or with ice-bath cooling. Salts of compound (I) may be obtained as crystals or amorphous substances according to the production methods. Amorphous substance can be prepared by adding the production methods to operations of freeze drying and the like, if necessary. Examples of the solvents to be used in these methods include alcohol solvents such as ethanol, 1-propanol and isopropanol; acetonitrile; ketone solvents such as acetone and 2-butanone; ester solvents such as ethyl acetate; saturated hydrocarbon solvents such as hexane and heptane; ether solvents such as t-butyl methyl ether or water. Each of these solvents may be used alone, or two or more may be mixed and used.

Methods for Producing Crystals of Compound (1) or Salts Thereof

A crystal of compound (I) or a salt thereof may be produced by the above-mentioned methods for producing compound (I) or a salt thereof, by heat-dissolving compound (I) or a salt thereof in a solvent and crystallizing it through cooling with stirring.

Compound (1) or the salt thereof to be used in the crystallization may be in any form: it may be a solvate, a hydrate, an anhydride, an amorphous substance, a crystalline substance (including those consisting of a plurality of crystalline polymorphs) or a combination thereof.

Examples of the solvents to be used in the crystallization include alcohol solvents such as methanol, ethanol, isopropanol and 1-propanol; acetonitrile; amide solvents such as N,N-dimethylformamide; ester solvents such as ethyl acetate; saturated hydrocarbon solvents such as hexane and heptane; ketone solvents such as acetone and 2-butanone; ether solvents such as t-butyl methyl ether or water. Furthermore, each of these solvents may be used alone, or two or more may be mixed and used.

The amount of the solvent to be used may be suitably selected, provided that the lower limit is the amount with which the compound (I) or the salt thereof is dissolved by heating or the suspension can be stirred, and that the upper limit is the amount with which the yield of the crystal is not significantly reduced.

A seed crystal (e.g., the crystal of the desired compound (I) or salt thereof) may be added or may not be added during the crystallization. The temperature at which the seed crystal is added is not particularly limited, but is preferably 0 to 80° C.

As the temperature to be employed when the compound (I) or salt thereof is dissolved by heating, that at which compound (I) or salt thereof dissolves may be suitably selected depending on the solvent, but it is preferably within the range between 50° C. to the temperature at which the recrystallization solvent starts to reflux, and more preferably 55 to 80° C.

Cooling during the crystallization could give substances containing different forms of crystals (polymorphism) in the case of rapid cooling. It is therefore desirable to perform the cooling while controlling the cooling rate as appropriate based on the consideration of its effect on the quality, grain size and the like of the crystal. Preferred is, for example, cooling at a cooling rate of 5 to 40° C./hour. More preferred is cooling at a cooling rate of, for example, 5 to 25° C./hour.

Furthermore, the final crystallization temperature may be selected suitably for the yield, quality and the like of the crystal, but is preferably −25 to 30° C.

The target crystal can be obtained by isolating the formed crystal through a conventional filtration procedure, washing the filtered-off crystal with a solvent if necessary, and further drying it. As the solvent to be used for washing the crystal, the same solvent as in the crystallization can be used. Preferably, it is, for example, ethanol, acetone, 2-butanone, ethyl acetate, diethyl ether, t-butyl methyl ether, hexane and the like. Each of these solvents may be used alone, or two or more may be mixed and used.

The crystal isolated through the filtration procedure may be dried appropriately by leaving it in air or under nitrogen flow, or by heating.

As the drying time, the time until the amount of residual solvent becomes less than the predefined amount may be selected as appropriate depending on the amount of production, the drying apparatus, the drying temperature and the like. Furthermore, drying may be performed under airflow or under reduced pressure. The degree of pressure reduction may be selected as appropriate depending on the amount of production, the drying apparatus, the drying temperature and the like. The obtained crystal may be left in air after drying if necessary.

The salts of compound (I) and the crystals thereof can be formulated by a conventional method, and examples of dosage forms include oral formulations (such as tablets, granules, powders, capsules and syrups), injections (for intravenous administration, intramuscular administration, subcutaneous administration and intraperitoneal administration) and external formulations (such as transdermal absorption formulations (such as ointments and patches), ophthalmic preparations, nasal preparations and suppositories).

For producing an oral solid formulation, a vehicle, a binder, a disintegrator, a lubricant, a colorant and the like can be added, if necessary, to the salts of compound (I) and the crystals thereof, and a tablet, a granule, a powder agent, or a capsule can be produced according to a conventional method. Moreover, such a tablet, a granule, a powder agent, a capsule or the like may be subjected to coating, if necessary.

Examples of the vehicle include lactose, crystalline cellulose and the like, examples of the binder include hydroxypropyl cellulose and the like, examples of the disintegrator include calcium sodium croscarmellose and the like, examples of the lubricant include magnesium stearate and the like, examples of the colorant include titanium oxide and the like, and examples of the coating agent include hydroxypropyl methyl cellulose and the like, but these components are not limited to the aforementioned examples.

The solid formulation such as a tablet, a capsule, a granule or a powder may usually contain any amount of the salts of compound (I) and the crystals thereof, so long as it exert efficacy to an extent of being applicable as a medicine.

For producing an injection (for intravenous administration, for intramuscular administration, for subcutaneous administration, for intraperitoneal administration, and for others), to the salts of compound (I) and the crystals thereof; if necessary, a pH regulator, a buffering agent, a suspending agent, a solubilizer, an antioxidant, a preservative (antiseptic), an isotonic agent, and the like are added, and an injection can be produced by a conventional method. The preparations may be lyophilized to be made extemporaneous dissolution-type lyophilized preparations.

As the pH regulator and the buffering agent, an organic acid or an inorganic acid and/or a salt thereof or the like, for example, can be used. As the suspending agent, hydroxypropyl cellulose or the like, for example, can be used. As the solubilizer, polysorbate 80 or the like, for example, can be used. As the antioxidant, α-tocopherol or the like, for example, can be used. As the preservative, methyl parahydroxybenzoate, ethyl parahydroxybenzoate or the like, for example, can be used. As the isotonic agent, glucose or the like, for example, can be used.

The injection formulation may usually contain any amount of the salts of compound (I) and the crystals thereof, so long as it exert efficacy to an extent of being applicable as a medicine.

For producing an external formulation, a basis raw material is added to the salts of compound (I) and the crystals thereof, and if necessary, for example, the preservative, the stabilizer, the pH regulator, the antioxidant, the colorant and the like described above are added, and for example, an endermic preparation (ointment, patch, and the like), eyedrops, nasal drops, suppository, and the like can be produced by conventional methods.

As basis raw materials to be used, various raw materials usually used, for example, for medicines, quasi-drugs and cosmetics can be used. Specific examples thereof include raw materials such as animal and vegetable oils, mineral oils, ester oils, waxes, emulsifiers, higher alcohols, fatty acids, silicon oils, surfactants, phospholipids, alcohols, polyhydric alcohols, water-soluble polymers, clay minerals and purified water.

The external preparation may usually contain any amount of the salts of compound (I) and the crystals thereof, so long as it exert efficacy to an extent of being applicable as a medicine.

A dose of the salts of compound (I) and the crystals thereof depends upon the level of symptom severity, the patients age, sex and weight, the administration form and the kind of salt, a specific kind of disease and the like, and is not especially limited unless it exceeds the maximum dose of the medicine that can be given without causing an unacceptable adverse reaction, and in an adult patient, it is administered, once or dividedly several times per day, at a dose for oral administration of generally approximately 30 μg to 10 g, specifically 100 μg to 5 g and more specifically 100 μg to 1 g, or a dose for injection administration of generally approximately 30 μg to 1 g, specifically 100 μg to 500 mg, and more specifically 100 μg to 300 mg.

EXAMPLE

Compounds according to the present invention can be produced by methods described in Production Examples and Examples described below, for example. However, these methods are mere examples, and therefore the compounds according to the present invention are not limited to those produced by specific examples described below in any cases.

In powder X-ray diffractometry of the crystals produced in the following Examples and Reference Examples, the resulting crystals were placed on a sample stage of a powder X-ray diffractometer and analyzed under the following conditions. FIGS. 1-3 and 6-15 show the results.

Measurement Conditions
Sample holder: aluminum
Target: copper
Detector: scintillation counter
Tube voltage: 50 kV
Tube current: 300 mA
Slit: DS 0.5 mm (Height limiting slit 2 mm), SS Open, RS Open
Scanning rate: 10°/min
Sampling interval: 0.02°
Scan range: 5 to 35°

Figure 4:
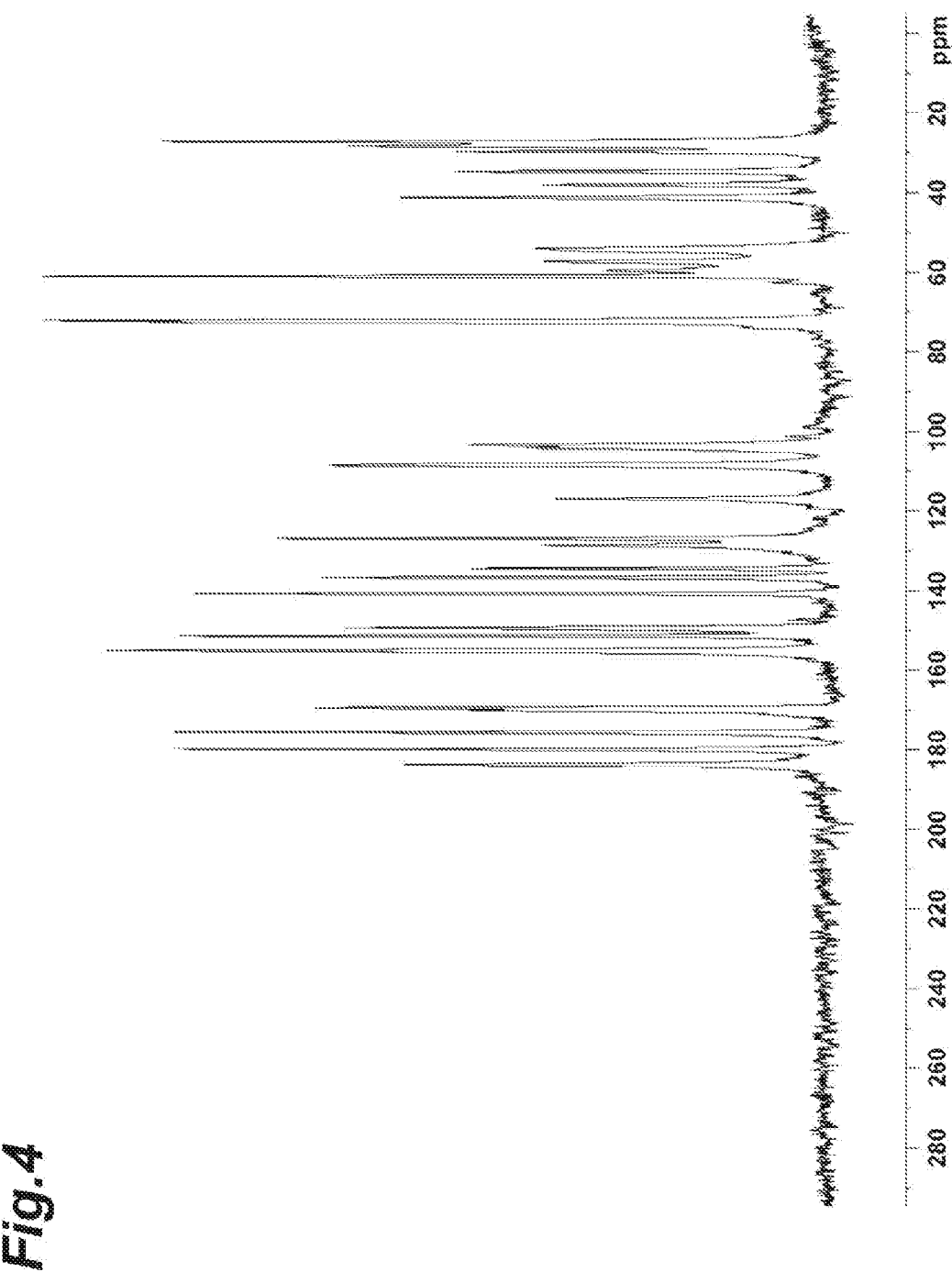
FIG. 4 is a $^{13}C$ solid state NMR spectrum of the crystal of the compound (I) 1.5 succinate salt obtained in Example 1.

The $^{13}$C solid-state NMR spectra of the crystals were measured under the following conditions. FIG. 4 shows the result.

Measurement Conditions
Apparatus used: AVANCE400 (from Bruker Corporation)
Measurement temperature: room temperature (22° C.)
Reference material: glycine (external reference: 176.03 ppm)
Measured nucleus: $^{13}$C (100.6248425 MHz)
Pulse repetition time: 3 seconds
Pulse mode: TOSS measurement In Production Examples, Silica gel 60 (Kanto Chemicals) or Presep Silica Gel (WAKO) was used as a purification silica gel used for silica gel column chromatography unless otherwise stated. In addition, NH silica gel (Fuji Silysia Chemical LTD.) or Hi-Flash Column Amino (YAMAZENE CORPORATION) was used as a purification silica gel used for NH silica gel column chromatography.

Varian Mercury 400, Varian Mercury Plus 400, Varian INOVA 500, or Avance 600 MHz (Bruker) was used for the measurement of proton nuclear magnetic resonance spectra, and the proton nuclear magnetic resonance spectra were measured at 400 MHz unless otherwise stated. Chemical shifts of proton nuclear magnetic resonance spectra are recorded in the unit of σ (ppm) with respect to tetramethylsilane and coupling constants are recorded in the unit of Hertz (Hz). Abbreviations for splitting patterns are as follows: s: singlet; d: doublet; t: triplet; m: multiplet; and brs: broad singlet.

In Production Examples, Examples and Reference Examples, commercially available products were appropriately used as commercially available compounds.

[Production Example 1-1]
N-(4-Chloropyridin-2-yl)acetamide

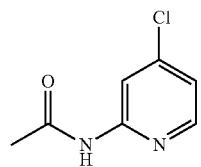

Commercially available 2-amino-4-chloropyridine (50 g, 389 mmol) was dissolved in acetic anhydride (500 mL), triethylamine (271 mL, 1.94 mol) was added at 20° C., and the mixture was stirred at 60° C. for 12 hours. The mixture was cooled to room temperature and then the solvent was evaporated. The residue was purified with silica gel column chromatography (n-heptane:ethyl acetate=4:1 to 1:1) and then the target fraction was concentrated under vacuum to obtain the title compound (66 g, 99%).

$^1$H-NMR Spectrum (CDCl$_3$) δ (ppm): 2.21 (3H, s), 7.05 (1H, dd, J=5.4, 1.9 Hz), 8.15 (1H, d, J=5.4 Hz), 8.30 (2H, brs).

[Production Example 1-2] Phenyl methylcarbamate

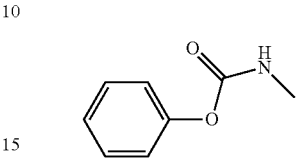

A mixture of commercially available methylamine hydrochloride (50 g, 0.74 mol), pyridine (124 mL, 1.53 mol), and N,N-dimethylformamide (500 mL) was stirred at 5° C., and commercially available phenyl chlorocarbonate (94 mL, 0.75 mol) was added dropwise over 2 hours. After the dripping was complete, the mixture was stirred under nitrogen atmosphere at room temperature for 16 hours. The reaction mixture was added to ice water (2 L) and extracted with ethyl acetate (1.5 L) twice. The organic layer was washed with water (1 L) and a saturated saline solution (300 mL). The organic layer was dried over anhydrous magnesium sulfate and then the solvent was evaporated. n-Heptane and ethyl acetate were added to the concentrated residue and the precipitate was collected by filtration and washed with n-heptane and tert-butyl methyl ether to obtain the title compound (74.2 g, 66%).

$^1$H-NMR Spectrum (CDCl$_3$) δ (ppm): 2.90 (3H, d, J=4.9 Hz), 4.95 (1H, brs), 7.08-7.16 (2H, m), 7.16-7.24 (1H, m), 7.31-7.41 (2H, m).

[Production Example 1-3]
1-(4-Phenylpiperidin-1-yl)ethanone

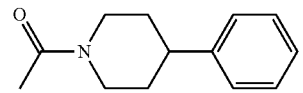

A mixture of commercially available 4-phenylpiperidine (10 g, 62 mmol), pyridine (5.7 mL, 70.5 mmol), and tetrahydrofuran (80 mL) was stirred at 0° C. and a mixture of acetyl chloride (5 mL, 70.3 mmol) and tetrahydrofuran (20 mL) was dripped over 10 minutes. The mixture was stirred under nitrogen atmosphere at 25° C. for 14 hours. Ethyl acetate (100 mL) and water (100 mL) were added to the reaction liquid for separation. The aqueous layer was extracted with ethyl acetate (100 mL), then the organic layers were combined, and the resultant was washed with a saturated aqueous sodium bicarbonate solution (100 mL), water (100 mL), and then a saturated saline solution (50 mL). The organic layer was dried over anhydrous magnesium sulfate and then the solvent was evaporated to obtain the title compound (12.3 g, 98%).

$^1$H-NMR Spectrum (CDCl$_3$) δ (ppm): 1.52-1.78 (2H, m), 1.81-1.99 (2H, m), 2.14 (3H, s), 2.63 (1H, td, J=12.9, 2.7 Hz), 2.74 (1H, tt, J=12.1, 3.7 Hz), 3.17 (1H, td, J=13.2, 2.6 Hz), 3.84-4.02 (1H, m), 4.69-4.89 (1H, m), 7.08-7.43 (5H, m).

[Production Example 1-4]
4-(1-Acetylpiperidin-4-yl)benzoic acid

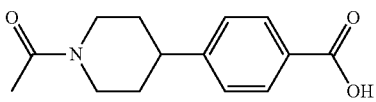

A mixture of aluminum chloride(III) (26 g, 195 mmol) and dichloromethane (200 mL) was stirred at 0° C., and oxalyl chloride (20 mL, 228 mmol) was dripped over 10 minutes. Then a mixture of 1-(4-phenylpiperidin-1-yl)ethanone described in Production Example 1-3 (12.3 g, 60.5 mmol) and dichloromethane (50 mL) was dripped over 30 minutes. The mixture was stirred under nitrogen atmosphere at 25° C. for 14 hours. The reaction liquid was poured onto ice and ethyl acetate (1 L) and water (1 L) were added for separation. The aqueous layer was extracted with ethyl acetate (1 L) twice, then the organic layer was washed with water (1 L) twice and then with a saturated saline solution (500 mL). The organic layer was dried over anhydrous magnesium sulfate and then the solvent was evaporated. Ethyl acetate was added to the concentrated residue and the product was collected by filtration and washed with ethyl acetate to obtain the title compound (9.09 g, 61%).

$^1$H-NMR Spectrum (CDCl$_3$) δ (ppm): 1.49-1.82 (2H, m), 1.92 (2H, t, J=13.2 Hz), 2.15 (3H, s), 2.65 (1H, t, J=11.7 Hz), 2.75-2.94 (1H, m), 3.08-3.30 (1H, m), 3.97 (1H, d, J=13.2 Hz), 4.82 (1H, d, J=12.8 Hz), 7.30 (2H, d, J=8.4 Hz), 8.05 (2, d, J=8.1 Hz).

[Production Example 1-5] 4-(Piperidin-4-yl)benzoic acid hydrochloride

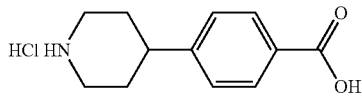

A mixture of 4-(1-acetylpiperidin-4-yl)benzoic acid described in Production Example 1-4 (4.50 g, 18.2 mmol) and 5 M hydrochloric acid (50 mL, 250 mmol) was stirred under nitrogen atmosphere at 140° C. for 18 hours. The mixture was cooled to room temperature and then the product was collected by filtration and washed with water to obtain the title compound (3.77 g, 86%).

$^1$H-NMR Spectrum (DMSO-d$_6$) δ (ppm): 1.60-2.15 (4H, m), 2.76-3.16 (3H, m), 3.27-3.45 (2H, m), 7.36 (2H, d, J=8.1 Hz), 7.92 (2H, d, J=8.1 Hz), 8.65-9.04 (2H, m), 12.89 (1H, brs).

[Production Example 1-6] 4-(1-(tert-Butoxycarbonyl)piperidin-4-yl)benzoic acid

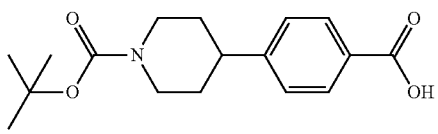 [SMILES: CC(C)(C)OC(=O)N1CCC(c2ccc(C(=O)O)cc2)CC1]

A mixture of 4-(piperidin-4-yl)benzoic acid hydrochloride described in Production Example 1-5 (2.00 g, 8.27 mmol), a 1 M sodium hydroxide solution (25 mL, 25 mmol), and acetone (50 mL) was stirred at 25° C., and a solution of di-tert-butyl dicarbonate (1.9 g, 8.71 mmol) in acetone (25 mL) was added dropwise over 10 minutes. The mixture was stirred under nitrogen atmosphere at 25° C. for 18 hours. 1 M hydrochloric acid (17 mL) was added under cooling at 0° C. The mixture was extracted with ethyl acetate (100 mL) twice. The organic layer was washed with a saturated saline solution (50 mL). The organic layer was dried over anhydrous magnesium sulfate and then concentrated under vacuum. n-Heptane and tert-butyl methyl ether were added to the concentrated residue and the product was collected by filtration and washed with n-heptane to obtain the title compound (2.30 g, 91%).

$^1$H-NMR Spectrum (CDCl$_3$) δ (ppm): 1.49 (9H, s), 1.57-1.76 (2H, m), 1.84 (2H, d, J=13.5 Hz), 2.62-2.97 (3H, m), 4.27 (2H, brs), 7.28-7.36 (2H, m), 7.98-8.10 (2H, m).

[Production Example 1-7] 3-Hydroxy-4-(2-methoxyethoxy)benzaldehyde

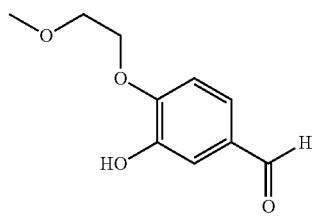

Commercially available 3,4-dihydroxybenzaldehyde (39.3 g, 285 mmol) and sodium carbonate (45.2 g, 427 mmol) were dissolved in N,N-dimethylformamide (400 mL), then commercially available 2-bromoethyl methyl ether (26.7 mL, 285 mmol) was added under nitrogen atmosphere at room temperature, and the mixture was stirred for 5 days. The mixture was cooled to 0° C. and then 2 M hydrochloric acid, ethyl acetate, and water were added for partition. The aqueous layer was extracted with ethyl acetate, then the combined organic layer was washed with a saturated saline solution and dried over anhydrous magnesium sulfate, and then filtered. The solvent was evaporated, dichloromethane was added, the precipitate was separated by filtration, and then the resultant filtrate was purified with silica gel column chromatography (n-heptane:ethyl acetate=17:3 to 1:1). The target fraction was concentrated under vacuum to obtain the title compound (12.9 g, 23%).

$^1$H-NMR Spectrum (CDCl$_3$) δ (ppm): 3.47 (3H, s), 3.76-3.80 (2H, m), 4.25-4.29 (2H, m), 6.40 (1H, brs), 7.01 (1H, d, J=8.4 Hz), 7.41 (1H, dd, J=8.2, 2.0 Hz), 7.45 (1H, d, J=1.8 Hz), 9.85 (1H, s).

[Production Example 1-8] 3-(Benzyloxy)-4-(2-methoxyethoxy)benzaldehyde

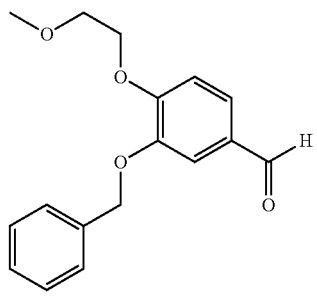 [SMILES: COCCOc1ccc(C=O)cc1OCc1ccccc1]

Potassium carbonate (11.8 g, 85.7 mmol) and benzyl chloride (10 mL, 86.9 mmol) were added to a liquid mixture of 3-hydroxy-4-(2-methoxyethoxy)benzaldehyde described in Production Example 1-7 (12.9 g, 65.9 mmol) in ethanol (130 mL) under nitrogen atmosphere at room temperature, and the mixture was heated under reflux at 90° C. for 2 hours. The mixture was cooled to 0° C. and then 2 M hydrochloric acid, ethyl acetate, and water were added for partition. The organic layer was washed with a saturated saline solution, dried over anhydrous magnesium sulfate, and then filtered. The solvent was evaporated and the resultant residue was purified with silica gel column chromatography (n-heptane:ethyl acetate=9:1 to 1:1). The target fraction was concentrated under vacuum to obtain the title compound (17.6 g, 93%).

$^1$H-NMR Spectrum (CDCl$_3$) δ (ppm): 3.46 (3H, s), 3.79-3.85 (2H, m), 4.24-4.30 (2H, m), 5.18 (2H, s), 7.03 (1H, d, J=8.1 Hz), 7.29-7.35 (1H, m), 7.35-7.41 (2H, m), 7.43-7.50 (4H, m), 9.82 (1H, s).

[Production Example 1-9] (E)-2-(Benzyloxy)-1-(2-methoxyethoxy)-4-(2-nitrovinyl)benzene

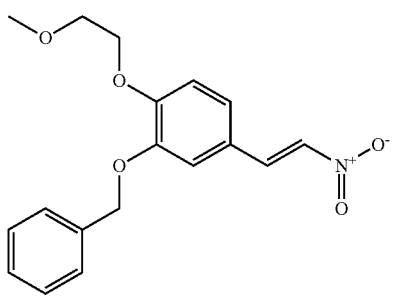 [SMILES: COCCOc1ccc(/C=C/[N+](=O)[O-])cc1OCc1ccccc1]

3-(Benzyloxy)-4-(2-methoxyethoxy)benzaldehyde described in Production Example 1-8 (17.6 g, 61.5 mmol) was dissolved in acetic acid (49.3 mL), then ammonium acetate (5.69 g, 73.8 mmol) and nitromethane (8.32 mL, 154 mmol) were added under nitrogen atmosphere at room temperature, and the mixture was heated under reflux at 130° C. for 2 hours. The mixture was cooled to room temperature and then the precipitate was collected by filtration and washed with ethanol to quantitatively obtain the title compound.

$^1$H-NMR Spectrum (CDCl$_3$) δ (ppm): 3.46 (3H, s), 3.78-3.84 (2H, m), 4.21-4.27 (2H, m), 5.16 (2H, s), 6.97 (1H, d, J=8.4 Hz), 7.06 (1H, d, J=1.8 Hz), 7.16 (1H, dd, J=8.4, 2.2 Hz), 7.30-7.48 (6H, m), 7.91 (1H, d, J=13.5 Hz).

[Production Example 1-10] 6-(2-Methoxyethoxy)-1H-indol-5-ol

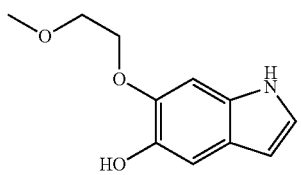

69% Nitric acid (15 mL, 233 mmol) was added to a mixture of (E)-2-(benzyloxy)-1-(2-methoxyethoxy)-4-(2-nitrovinyl)benzene described in Production Example 1-9 (20.2 g, 61.5 mmol) and acetic acid (120 mL) at 25° C., and the mixture was stirred at room temperature for 6 hours. The reaction mixture was poured onto ice, and the precipitate was collected by filtration and then washed with water to obtain a crude product (23.0 g). The crude product (23.0 g) was suspended in methanol (500 mL), then 10% palladium-carbon (water content, 50%) (8 g) was added at room temperature, and the mixture was stirred under hydrogen atmosphere for 6 hours. The catalyst was filtered off with celite, the filtrate was concentrated under vacuum, and the resultant was purified with silica gel column chromatography (n-heptane:ethyl acetate=2:1 to 1:1). The target fraction was concentrated under vacuum to obtain the title compound (3.94 g, 31%).

$^1$H-NMR Spectrum (CDCl$_3$) δ (ppm): 3.48 (3H, s), 3.69-3.78 (21, m), 4.16-4.23 (2H, m), 6.24 (1H, s), 6.41 (1H, ddd, J=3.1, 2.1, 0.8 Hz), 6.97 (1H, s), 7.10 (1H, dd, J=3.2, 2.5 Hz), 7.15 (1H, s), 7.94 (1H, brs).

[Production Example 1-11] N-(4-((6-(2-Methoxyethoxy)-1H-indol-5-yl)oxy)pyridin-2-yl)acetamide

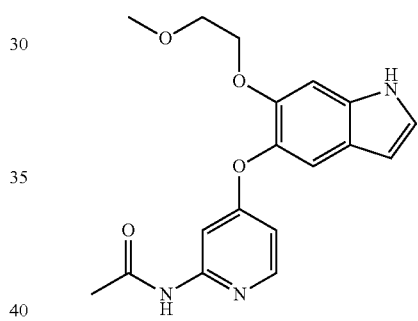

6-(2-Methoxyethoxy)-1H-indol-5-ol described in Production Example 1-10 (3.94 g, 19.0 mmol) and N-(4-chloropyridin-2-yl)acetamide described in Production Example 1-1 (3.25 g, 19.0 mmol) were dissolved in dimethylsulfoxide (25 mL), then 97% potassium tert-butoxide (2.20 g, 19.0 mmol) was added at room temperature, and the mixture was heated and stirred at 150° C. for 13 hours. Water and ethyl acetate were added to the reaction liquid at room temperature for partition. The aqueous layer was extracted with ethyl acetate three times and the combined organic layer was washed with water. The organic layer was dried over anhydrous sodium sulfate. The drying agent was filtered off and the filtrate was concentrated under vacuum, and then the resultant was purified with NH silica gel column chromatography (n-heptane:ethyl acetate=2:3 to 0:1—ethyl acetate::methanol=49:1 to 9:1). The target fraction was concentrated under vacuum to obtain the title compound (3.45 g, 53%).

$^1$H-NMR Spectrum (500 MHz, CDCl$_3$) δ (ppm): 2.13 (3H, s), 3.27 (3H, s), 3.54-3.58 (2H, m), 4.07-4.11 (2H, m), 6.46-6.50 (1H, m), 6.54 (1H, dd, J=5.8, 1.9 Hz), 7.05 (1H, s), 7.14-7.17 (1H, m), 7.36 (1H, s), 7.75 (1H, brs), 8.02 (1H, d, J=5.8 Hz), 8.10 (1H brs), 8.19 (1H, brs).

[Production Example 1-12] 4-((6-(2-Methoxy-ethoxy)-1H-indol-5-yl)oxy)pyridin-2-amine

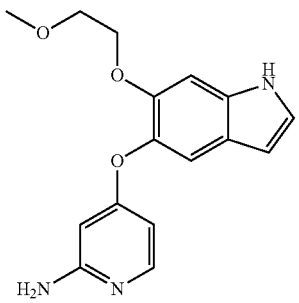 [SMILES: COCCOc1cc2[nH]ccc2cc1Oc1ccnc(N)c1]

N-(4-((6-(2-methoxyethoxy)-1H-indol-5-yl)oxy)pyridin-2-yl)acetamide described in Production Example 1-11 (3.45 g, 10.1 mmol) was dissolved in methanol (50 mL), a 2 M sodium hydroxide solution (50 mL) was added at room temperature, and the mixture was heated and stirred at 70° C. for 3 hours. Water and ethyl acetate were added to the reaction mixture for partition. The aqueous layer was extracted with ethyl acetate three times and the combined organic layer was dried over anhydrous sodium sulfate. The drying agent was filtered off and the filtrate was concentrated under vacuum and the resultant was purified with NH silica gel column chromatography (n-heptane:ethyl acetate=3:7 to 0:1—ethyl acetate:methanol=49:1 to 24:1). The target fraction and the mixture fraction were concentrated under vacuum separately from each other, the mixture fraction was purified again with silica gel column chromatography (ethyl acetate:methanol=1:0 to 9:1), and then the resultant was combined with the above-described target fraction to obtain the title compound (2.60 g, 86%).

$^1$H-NMR Spectrum (500 MHz, CDCl$_3$) δ (ppm): 3.31 (3H, s), 3.58-3.63 (2H, m), 4.08-4.11 (2H, m), 4.28 (2H, brs), 5.90 (1H, d, J=2.4 Hz), 6.29 (1H, dd, J=6.1, 2.2 Hz), 6.44-6.52 (1H, m), 7.06 (1H, s), 7.15-7.20 (1H, m), 7.34 (1H, s), 7.88 (1H, d, J=5.8 Hz), 8.22 (1H, brs).

[Production Example 1-13] 5-[(2-Aminopyridin-4-yl)oxy]-6-(2-methoxyethoxy)-N-methyl-1H-indole-1-carboxamide

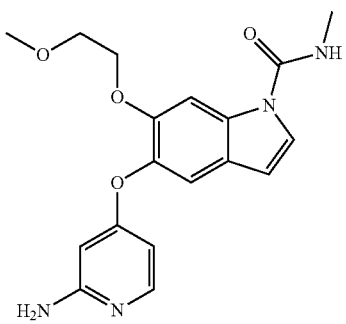

4-((6-(2-Methoxyethoxy)-1H-indol-5-yl)oxy)pyridin-2-amine described in Production Example 1-12 (2.60 g, 8.67 mmol) was dissolved in N,N-dimethylformamide (50 mL), then 50-72% oily sodium hydride (499 mg) was added under nitrogen atmosphere at room temperature. Phenyl methyl-carbamate described in Production Example 1-2 (1.97 g, 13.0 mmol) was added, and the mixture was stirred at room temperature for 1 hour. The reaction mixture was cooled to 0° C. and ethyl acetate and water were added for partition. The aqueous layer was extracted with ethyl acetate twice, sodium chloride was added to the aqueous layer, and the resultant was extracted with ethyl acetate three times. The combined organic layer was dried over anhydrous sodium sulfate. The drying agent was filtered off and the filtrate was concentrated under vacuum, and then the resultant was purified with NH silica gel column chromatography (n-heptane:ethyl acetate=1:4 to 0:1—ethyl acetate:methanol=49:1 to 24:1). The target fraction was concentrated under vacuum, and ethyl acetate was added and the precipitate was collected by filteration and washed to obtain the title compound (2.23 g, 72%).

$^1$H-NMR Spectrum (500 MHz, CDCl$_3$) δ (ppm): 3.06 (3H, d, J=4.9 Hz), 3.29 (3H, s), 3.59-3.63 (2H, m), 4.14-4.17 (2H, m), 4.30 (2H, brs), 5.52-5.59 (1H, m), 5.89 (1H, d, J=2.4 Hz), 6.27 (1H, dd, J=5.8, 1.9 Hz), 6.55 (1H, d, J=3.9 Hz), 7.27-7.29 (2H, m), 7.89 (1H, d, J=5.9 Hz), 7.99 (1H, s).

[Production Example 1-14] 6-(2-Methoxyethoxy)-N-methyl-5-{[2-({[4-(piperidin-4-yl)phenyl]carbonyl}amino)pyridin-4-yl]oxy}-1H-indole-1-carboxamide

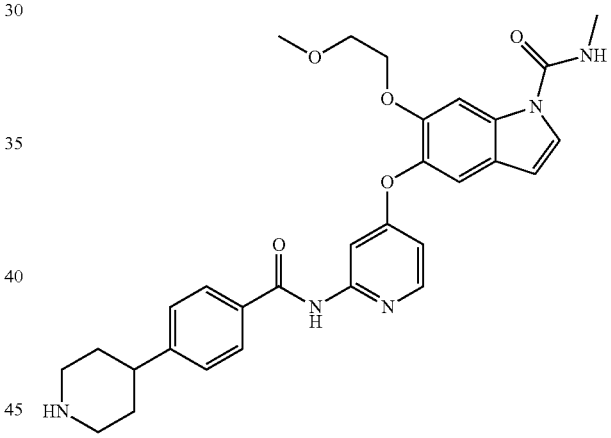

Benzotriazole (609 mg, 5.11 mmol) was dissolved in dichloromethane (25 mL), thionyl chloride (373 μL, 5.11 mmol) was added under nitrogen atmosphere at room temperature, and the mixture was stirred for 5 minutes. 4-(1-(tert-Butoxycarbonyl)piperidin-4-yl)benzoic acid described in Production Example 1-6 (1.3 g, 4.26 mmol) was added to the reaction mixture at room temperature, and the mixture was stirred for 30 minutes. The reaction mixture was filtered through a glass filter entirely covered with anhydrous sodium sulfate and the resultant was washed with dichloromethane, the filtrate was added to a mixture of 5-[(2-aminopyridin-4-yl)oxy]-6-(2-methoxyethoxy)-N-methyl-1H-indole-1-carboxamide described in Production Example 1-13 (0.95 g, 2.67 mmol), triethylamine (1.86 mL, 13.3 mmol), and 4-dimethylaminopyridine (16 mg, 0.133 mmol) in N,N-dimethylformamide (3 mL) and dichloromethane (20 mL) at 0° C. over 5 minutes, and the mixture was rinsed with dichloromethane (10 mL) and then stirred at the same temperature for 5 minutes. The mixture was stirred at room temperature for 2 hours, then a 40% aqueous methylamine solution (2.3 mL, 26.7 mmol) was added, and then the mixture was stirred at room temperature for 1.5 hours. A saturated aqueous sodium bicarbonate solution was added to the reaction mixture for partition and the aqueous layer was extracted with ethyl acetate three times. The combined organic layer was dried over anhydrous sodium sulfate. The drying agent was filtered off, then the filtrate was concentrated under vacuum and the resultant was purified with silica gel column chromatography (n-heptane:ethyl acetate=1:1 to 0:1—ethyl acetate:methanol=49:1 to 23:2) to obtain a crude product (1.11 g).

The crude product (1.11 g) was dissolved in dichloromethane (50 mL) and trifluoroacetic acid (5.0 mL) was added at room temperature. The mixture was stirred at room temperature for 30 minutes, then the resultant was concentrated under vacuum, and then the residue was dissolved in dichloromethane and triethylamine and the resultant was concentrated under vacuum. The residue was purified with NH silica gel column chromatography (ethyl acetate:methanol=1:0 to 22:3) to obtain the title compound (829 mg, 57%).

$^1$H-NMR Spectrum (500 MHz, CDCl$_3$) δ (ppm): 1.59-1.69 (21H, m), 1.83 (2H, d, J=14.1 Hz), 2.68 (1H, tt, J=12.0, 3.6 Hz), 2.75 (2H, td, J=12.2, 2.4 Hz), 3.04 (3H, d, J=4.9 Hz), 3.17-3.23 (2H, m), 3.26 (3H, s), 3.55-3.61 (2H, m), 4.15-4.21 (2H, m), 5.57-5.65 (1H, m), 6.53 (1H, d, J=3.4 Hz), 6.62 (1H dd, J=5.8, 2.4 Hz), 7.25 (1H, d, J=3.9 Hz), 7.30-7.34 (3H, m), 7.77-7.82 (2H, m), 7.91 (1H, d, J=2.4 Hz), 8.02 (1H, s), 8.10 (1H, d, J=5.9 Hz), 8.50 (1H, brs).

[Production Example 1-15] 5-({2-[({4-[1-(2-Hydroxyethyl)piperidin-4-yl]phenyl}carbonyl)amino]pyridin-4-yl}oxy)-6-(2-Methoxyethoxy)-N-methyl-1H-indole-1-carboxamide

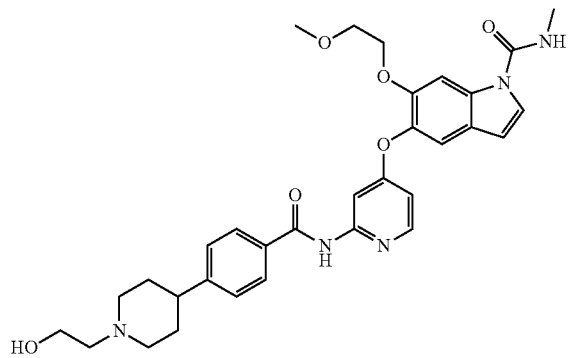 [SMILES: CNC(=O)n1ccc2cc(Oc3ccnc(NC(=O)c4ccc(C5CCN(CCO)CC5)cc4)c3)c(OCCOC)cc21]

Sodium triacetoxyborohydride (114 mg, 0.54 mmol) and commercially available 2-hydroxyacetaldehyde (34.4 mg, 0.57 mmol) were added to a mixture of 6-(2-methoxyethoxy)-N-methyl-5-{[2-({[4-(piperidin-4-yl)phenyl]carbonyl}amino)pyridin-4-yl]oxy}-1H-indole-1-carboxamide described in Production Example 1-14 (100 mg, 0.18 mmol) and tetrahydrofuran (4 mL) at room temperature, and the mixture was stirred at room temperature for 2 hours. A saturated aqueous sodium bicarbonate solution and ethyl acetate were added to the reaction mixture for partition. The aqueous layer was extracted with ethyl acetate, and the combined organic layer was washed with a saturated saline solution, then dried over anhydrous sodium sulfate, and then filtered. The solvent was evaporated and the resultant residue was purified with NH silica gel column chromatography (ethyl acetate:methanol=1:0-97:3-9:1). The target fraction was concentrated under vacuum, then the precipitate was collected by filtration and washed with a liquid mixture of diethyl ether and n-hexane to obtain the title compound (90 mg, 83%). Typical powder X-ray diffraction angles of the obtained compound (free form of the compound (I) (Free Form A)) are shown below. (2θ±0.2°): 10.4°, 10.9°, 11.4°, 13.5°, 16.1°, 19.7°, 20.4°, 21.5°, 23.3° and 24.3°.

$^1$H-NMR Spectrum (CDCl$_3$) δ (ppm): 1.70-1.92 (4H, m), 2.15-2.24 (2H, m), 2.53-2.65 (3H, m), 3.01-3.09 (5H, m), 3.26 (3H, s), 3.56-3.60 (2H, m), 3.64 (2H, t, J=5.2 Hz), 4.15-4.20 (2H, m), 5.49-5.54 (1H, m), 6.55 (1H, d, J=3.7 Hz), 6.61 (1H, dd, J=5.8, 2.3 Hz), 7.24-7.28 (1H, m), 7.30-7.35 (3H, m), 7.81 (2H, d, J=8.2 Hz), 7.91 (1H, d, J=2.4 Hz), 8.01 (1H, s), 8.10 (11H, d, J=5.9 Hz), 8.50 (1H, brs).

Example 1

Preparation of a crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 1.5 succinate salt (another name: 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide=butanedioate (2:3))

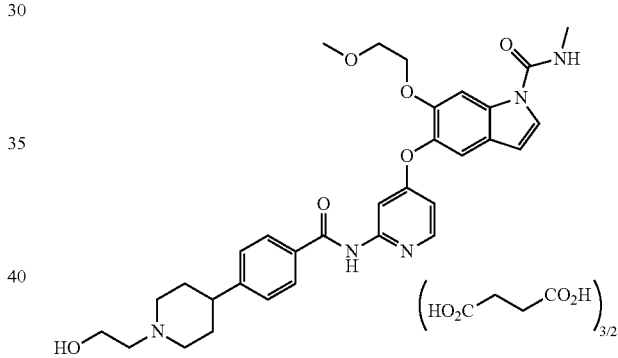

2.93 g of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide described in Production Example 1-15 was weighed in a recovery flask, 60 mL of ethanol was added, and the mixture was heated and stirred at 70° C. in an oil bath to be dissolved. Succinic acid (1.23 g) was added, then turned off the oil bath and gradually cooled. The mixture was stirred at room temperature for 2 hours, and further stirred at 5° C. for 1 hour. The solid was collected by filtration to obtain the title compound (3.70 g).

$^1$H-NMR Spectrum (600 MHz, CD$_3$OD) δ (ppm): 1.96-2.10 (4H, m), 2.52 (6H, s), 2.93 (1H, m), 2.96 (3H, s), 3.01 (2H, m), 3.16 (2H, t, J=5.4 Hz), 3.22 (3H, s), 3.56 (2H, t, J=4.7 Hz), 3.61 (2H, m), 3.87 (2H, t, J=5.4 Hz), 4.14 (2, t, J=4.6 Hz), 6.61 (1H, d, J=3.6 Hz), 6.68 (1H, dd, J=5.8, 2.3 Hz), 7.37 (1H, s), 7.42 (2H, d, J=8.3 Hz), 7.58 (1H, d, J=3.6 Hz), 7.73 (1H, d, J=2.2 Hz), 7.88 (2H, d, J=8.3 Hz), 8.08 (1H, s), 8.15 (1H, d, J=5.8 Hz).

$^{13}$C-NMR (100 MHz, solid state) δ (ppm): 27.1, 28.3, 29.7, 34.8, 38.0, 41.3, 54.0, 57.3, 59.7, 60.9, 72.1, 72.5, 103.3, 104.2, 108.5, 116.9, 126.9, 128.6, 134.5, 136.7, 140.7, 149.4, 151.3, 155.1, 169.5, 170.1, 175.6, 179.9, 183.7.

Example 2

Preparation of a crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 0.5 succinate salt (α)

117 mg of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide described in Production Example 1-15 and succinic acid (11.8 mg) were added to a 30 mL recovery flask, a solution of 2 mL of isopropanol/water (8/2, v/v) was added, ultrasound irradiation was conducted, and the mixture was stirred at room temperature for 2-3 hours. The solid was collected by filtration to obtain the title compound (77.5 mg).

$^1$H-NMR Spectrum (600 MHz, CD$_3$OD) δ (ppm): 1.86-2.00 (4H, m), 2.51 (2H, s), 2.62 (2H, m), 2.79 (1H, m), 2.87 (2H, t, J=5.5 Hz), 2.96 (3H, s), 3.22 (3H, s), 3.36 (2H, d, J=11.8 Hz), 3.56 (2H, t, J=4.6 Hz), 3.79 (2H, t, J=5.7 Hz), 4.15 (2H, t, J=4.6 Hz), 6.61 (1H, d, J=3.6 Hz), 6.68 (1H, dd, J=5.7, 2.1 Hz), 7.37 (1H, s), 7.40 (2H, d, J=8.2 Hz), 7.58 (1H, d, J=3.6 Hz), 7.73 (1H, d, J=2.0 Hz), 7.86 (2H, d, J=8.3 Hz), 8.08 (1H, s), 8.14 (1H, d, J=5.8 Hz).

Example 3

Preparation of a crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide maleate salt Maleic acid (24.1 mg) and 2 mL of acetone were added to 101 mg of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide described in Production Example 1-15, and the mixture was stirred at room temperature overnight. The solid was collected by filtration to obtain the title compound (113 mg).

Example 4

Preparation of a crystal of 5-({2-[({4-[1-(2-hydroxyethyl)piperidin-1-yl]phenyl}carbonyl)amino]pyridin-4-yl}oxy)-6-(2-methoxyethoxy)-N-methyl-1H-indole-1-carboxamide 0.5 succinate salt (α)

550 mg of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide, succinic acid (55.3 mg) and water (5.5 ml) were added to a test tube, and ultrasound irradiation was conducted, and then the mixture was stirred at room temperature overnight. The solid was filtered for overnight. The solid was ground in an agate mortar, and stored under the condition of 40° C./75% RH for approximately 1.5 hours, and then the title compound (620 mg) was obtained.

$^1$H-NMR Spectrum (CD$_3$OD) δ (ppm): 1.86-2.00 (4H, m), 2.51 (2H, s), 2.62 (2H, m), 2.79 (1H, m), 2.87 (2H, brt, J=5.5 Hz), 2.96 (3H, s), 3.22 (3H, s), 3.36 (2H, brd, J=11.8 Hz), 3.56 (2H, brt, J=4.6 Hz), 3.79 (2H, t, J=5.7 Hz), 4.15 (2H, brt, J=4.6 Hz), 6.61 (1H, d, J=3.6 Hz), 6.68 (1H, dd, J=5.7, 2.1 Hz), 7.37 (1H, s), 7.40 (2H, d, J=8.2 Hz), 7.58 (1H, d, J=3.6 Hz), 7.73 (1H, d, J=2.0 Hz), 7.86 (2H, d, J=8.3 Hz), 8.08 (1H, s), 8.14 (1H, d, J=5.8 Hz).

Example 5

Preparation of a crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 0.5 succinate salt (β)

The sample obtained in Example 4 was dried under reduced pressure for 3 days to obtain the title compound.

$^1$H-NMR Spectrum (CD$_3$OD) δ (ppm): 1.87-2.00 (4H, m), 2.51 (2H, s), 2.65 (2H, m), 2.79 (1H, m), 2.89 (2H, brt, J=5.6 Hz), 2.95 (3H, s), 3.22 (3H, s), 3.38 (2H, brd, J=12.1 Hz), 3.56 (2H, m), 3.80 (2H, t, J=5.6 Hz), 4.14 (2H, m), 6.60 (1H, d, J=3.7 Hz), 6.67 (1H, dd, J=5.8, 2.3 Hz), 7.37 (1H, s), 7.40 (2H, d, J=8.4 Hz), 7.57 (1H, d, J=3.7 Hz), 7.73 (1H, d, J=2.3 Hz), 7.86 (2H, d, J=8.4 Hz), 8.08 (1H, s), 8.14 (1H, d, J=5.8 Hz).

Example 6

Preparation of an amorphous of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 1.5 succinate salt 251 mg of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 1.5 succinate salt was dissolved in 25 mL of 50% tert-Butyl alcohol aqueous solution. 3 mL of the sample solution was added to a test tube, and the sample solution was frozen in ethanol cooled with dry ice. The solvent was removed on the lyophilizer to obtain the title compound (30.8 mg).

$^1$H-NMR Spectrum (CD$_3$OD) δ (ppm): 1.96-2.11 (4H, m), 2.53 (6H, s), 2.93 (1H, m), 2.96 (3H, s), 3.00 (2H, m), 3.15 (2H, t, J=5.4 Hz), 3.22 (3H, s), 3.56 (2H, m), 3.60 (2H, brd, J=12.4 Hz), 3.87 (2H, t, J=5.5 Hz), 4.15 (2H, brt, J=4.6 Hz), 6.61 (1H, d, J=3.7 Hz), 6.68 (1H, brd, J=3.8 Hz), 7.37 (1H, s), 7.42 (2H, d, J=8.3 Hz), 7.58 (1H, d, J=3.8 Hz), 7.73 (1H, brs), 7.88 (2H, d, J=8.3 Hz), 8.08 (1H, s), 8.15 (1H, brd, J=5.0 Hz).

Reference Example 1

Preparation of a crystal of 5-({2-[({4-[1-(2-hydroxyethyl)piperidin-4-yl]phenyl}carbonyl)amino]pyridin-4-yl}oxy)-6-(2-methoxyethoxy)-N-methyl-H-indole-1-carboxamide (Free Form B)

93.2 mg of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide described in Production Example 1-15 was weighed in a test tube, then 2.99 mL of isopropanol and 264 μL of water were added. The mixture was heated at 70-100° C. in an oil bath to be dissolved. The resultant solution was stirred at −5° C. in a thermostat control bath for 16 hours. The precipitated solid was collected by filtration and dried under reduced pressure for overnight to obtain the title compound. Typical powder X-ray diffraction angles of the obtained compound are shown below. (2θ±0.2°): 7.8°, 10.8°, 13.10, 14.20, 17.8°, 21.5°, 21.7°, 23.4°, 24.5° and 29.0°.

Reference Example 2

Preparation of a crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide (Free Form Hydrate)

2 ml of isopropanol and 2 ml of water were added to 208 mg of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide described in Production Example 1-15. After ultrasound irradiation was conducted in ice water, the mixture was stirred at 5° C. for 3 days. The suspended solid was collected by filtration to obtain the title compound (106 mg). Typical powder X-ray diffraction angles of the obtained compound are shown below. (2θ±0.2°): 8.8°, 9.6°, 15.2°, 16.3°, 20.00°, 20.80°, 21.40, 22.00°, 23.80 and 27.1°.

Reference Example 3

Preparation of a crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide mesylate salt 2 ml of acetone was added to 30.1 mg of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide described in Production Example 1-15, then methanesulfonic acid (4.0 µl) was added, and stirred at room temperature for 4 days. The solid was collected by filtration to obtain the title compound (20.4 mg). Typical powder X-ray diffraction angles of the obtained compound are shown below. (2θ±0.2°): 11.7°, 13.7, 15.20, 16.9°, 18.00, 18.7°, 19.9°, 21.1°, 22.00 and 24.1°.

Reference Example 4

Preparation of a crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide tosylate salt 2 ml of acetone was added to 30.7 mg of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide described in Production Example 1-15, then p-toluenesulfonic acid monohydrate (12.3 mg) was added, and stirred at room temperature for 4 days. The solid was collected by filtration to obtain the title compound (15.1 mg). Typical powder X-ray diffraction angles of the obtained compound are shown below. (2θ±0.2°): 11.9°, 12.6°, 13.5°, 13.80, 17.60, 18.0°, 18.6, 20.4°, 21.40 and 23.3°.

Reference Example 5

Preparation of a crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide benzoate salt 0.2 ml of ethyl acetate was added to a mixture of 20.3 mg of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide described in Production Example 1-15 and benzoic acid (8.91 mg) and stirred at room temperature. After 2 hours, 0.1 ml of ethyl acetate was added, and the reaction mixture was further stirred overnight. The solid was collected by filtration to obtain the title compound. Typical powder X-ray diffraction angles of the obtained compound are shown below. (2θ0.20): 9.30°, 13.90, 14.5, 15.8°, 18.10, 19.4°, 20.5°, 21.30, 22.60 and 26.20.

Reference Example 6

Preparation of a crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide fumarate salt 2 ml of acetone was added to a mixture of 30.6 mg of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide described in Production Example 1-15 and fumaric acid (7.24 mg), and stirred at room temperature overnight. The solid was collected by filtration to obtain the title compound. Typical powder X-ray diffraction angles of the obtained compound are shown below. (2θ±0.20): 9.60, 13.8°, 15.7°, 16.70, 19.80, 21.0°, 22.0°, 22.4°, 24.7° and 25.7°.

Reference Example 7

Preparation of a crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide hydrochloride salt 2 ml of acetone and 6N hydrochloric acid (10.0 µl) were added to 29.5 ml of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide described in Production Example 1-15, and the reaction mixture was stirred at room temperature. The title compound was isolated from the solvent as oil form.

Reference Example 8

Preparation of a crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide hydrobromide salt 2 ml of acetone and hydrobromic acid (7.8 µl) were added to 32.7 mg of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide described in Production Example 1-15, and the reaction mixture was stirred at room temperature. The title compound was isolated from the solvent as oil form.

Test Example

The following Test Examples were carried out and physical properties or pharmacological effects of the compound (I) described in Production Example 1-15 or the salts of compound (I) and the crystals thereof were assessed

[Test Example 1] Hygroscopicity

Figure 5:
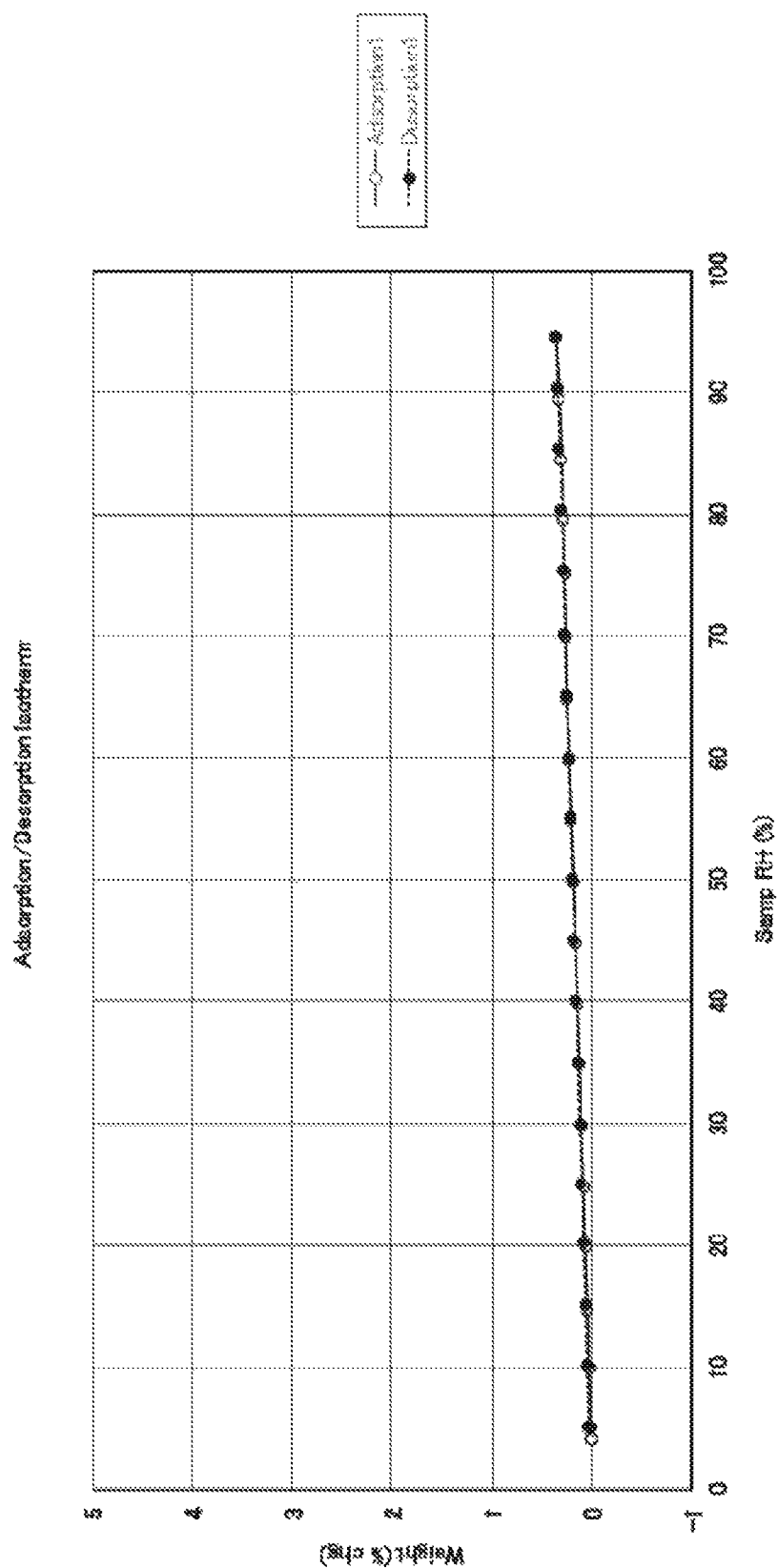
FIG. 5 is a hygroscopicity pattern of the crystal of the compound (I) 1.5 succinate salt obtained in Example 1. The abscissa shows relative humidity and the ordinate shows weight change.
Figure 6:
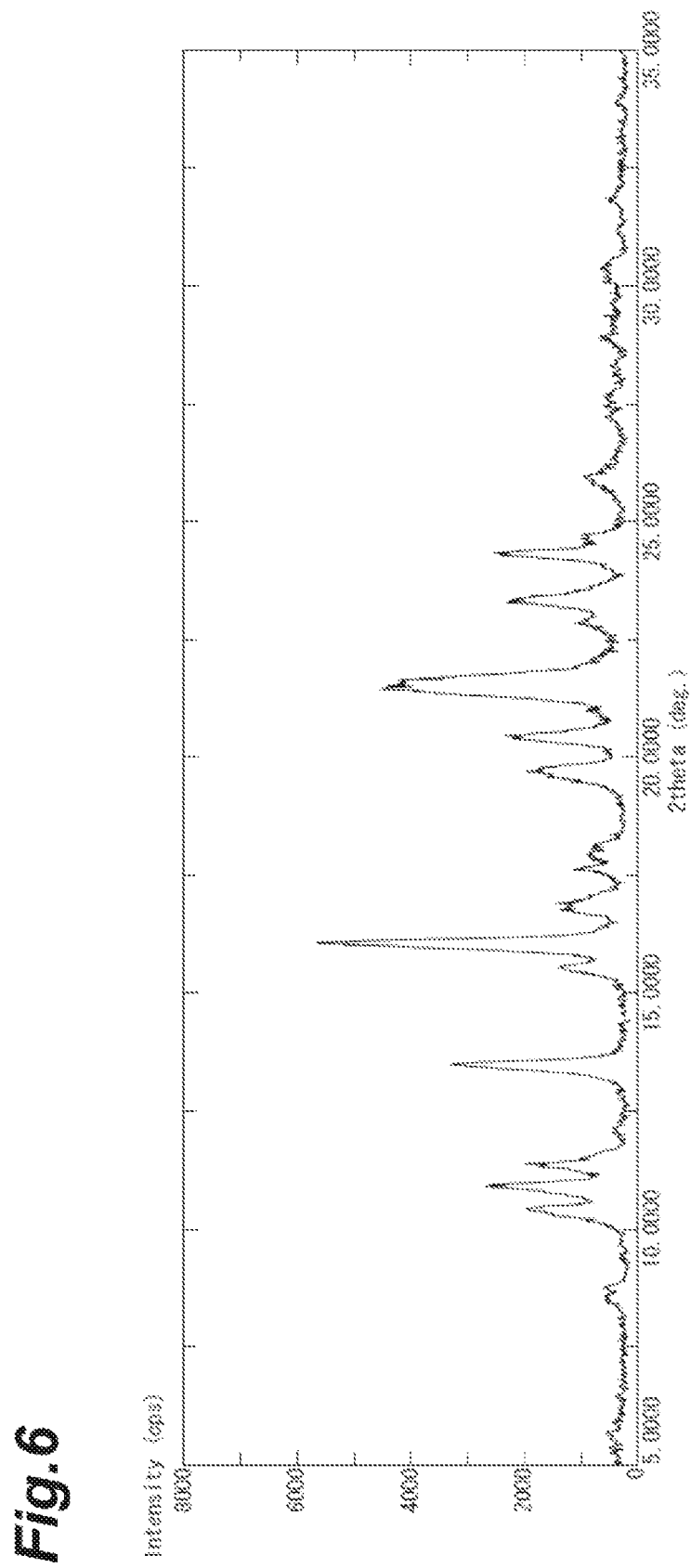
FIG. 6 is a powder X-ray diffraction pattern of the crystal of free form of the compound (I) (Free Form A) obtained in Preparation Example 1-15. The abscissa shows the diffraction angle (2θ) and the ordinate shows the peak intensity.
Figure 7:
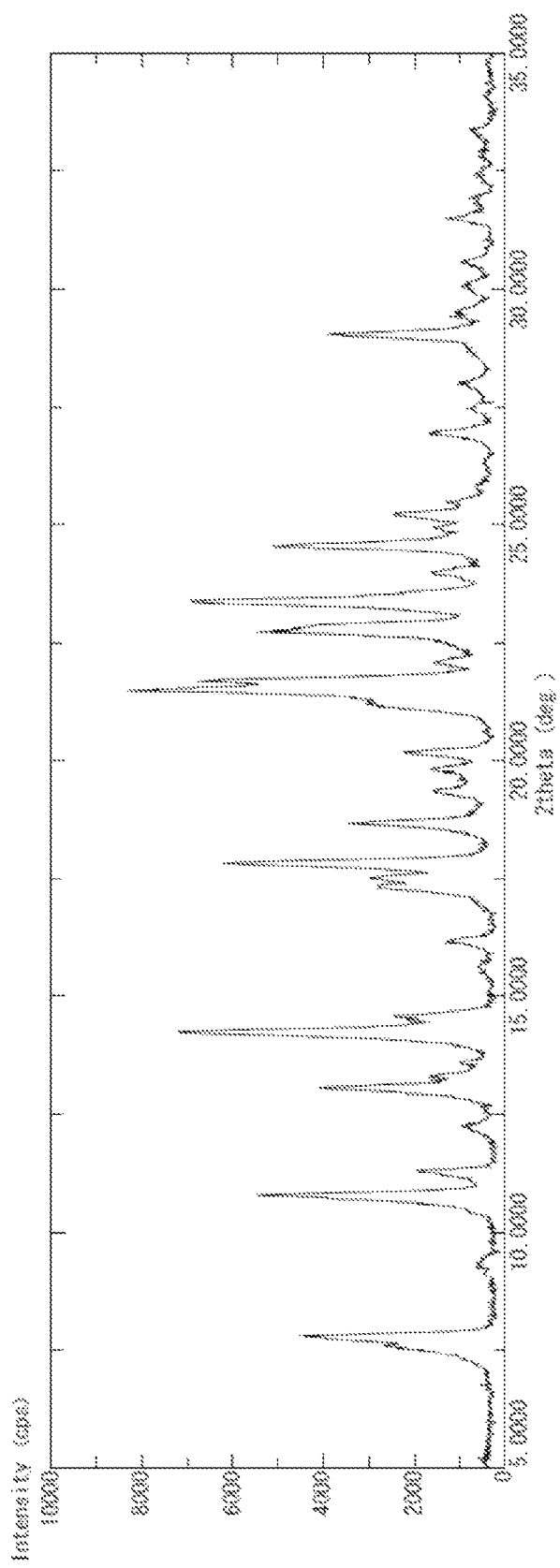
FIG. 7 is a powder X-ray diffraction pattern of the crystal of free form of the compound (I) (Free Form B) obtained in Reference Example 1. The abscissa shows the diffraction angle (2θ) and the ordinate shows the peak intensity.
Figure 8:
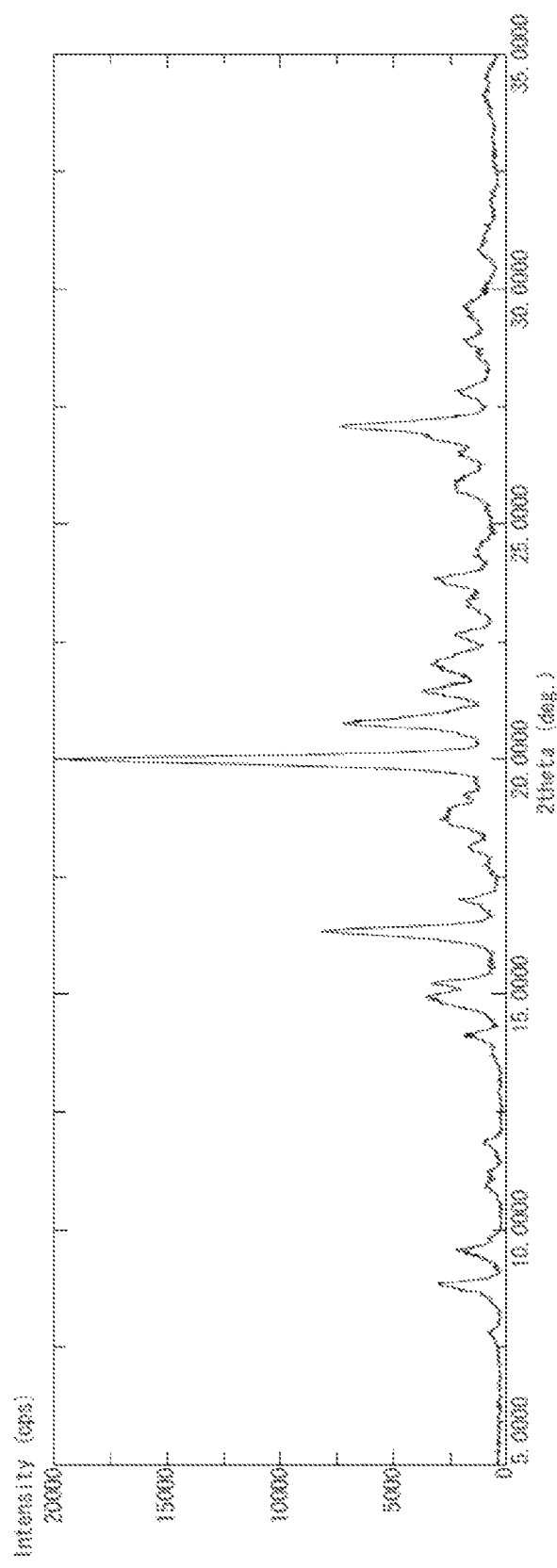
FIG. 8 is a powder X-ray diffraction pattern of the crystal of free form of the compound (i) (Free Form Hydrate) obtained in Reference Example 2. The abscissa shows the diffraction angle (2θ) and the ordinate shows the peak intensity.
Figure 9:
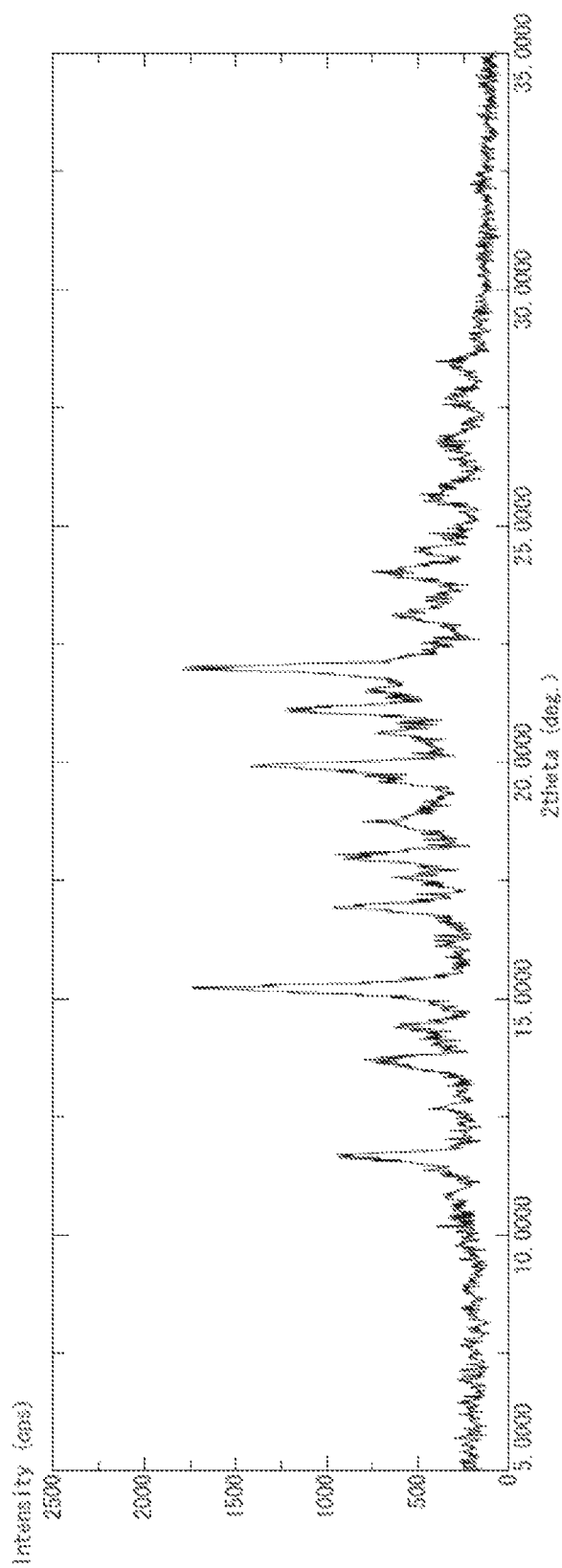
FIG. 9 is a powder X-ray diffraction pattern of the crystal of compound (I) mesylate salt obtained in Reference Example 3. The abscissa shows the diffraction angle (2θ) and the ordinate shows the peak intensity.
Figure 10:
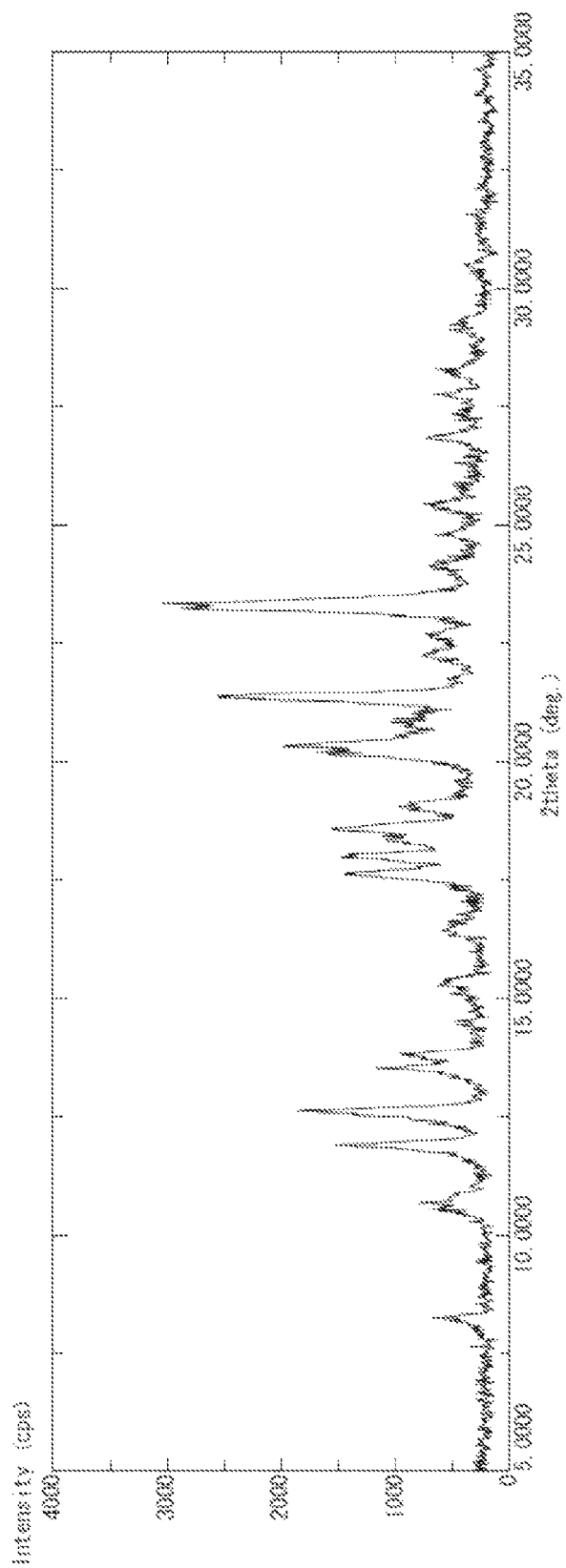
FIG. 10 is a powder X-ray diffraction pattern of the crystal of the compound (I) tosylate salt obtained in Reference Example 4. The abscissa shows the diffraction angle (2θ) and the ordinate shows the peak intensity.
Figure 11:
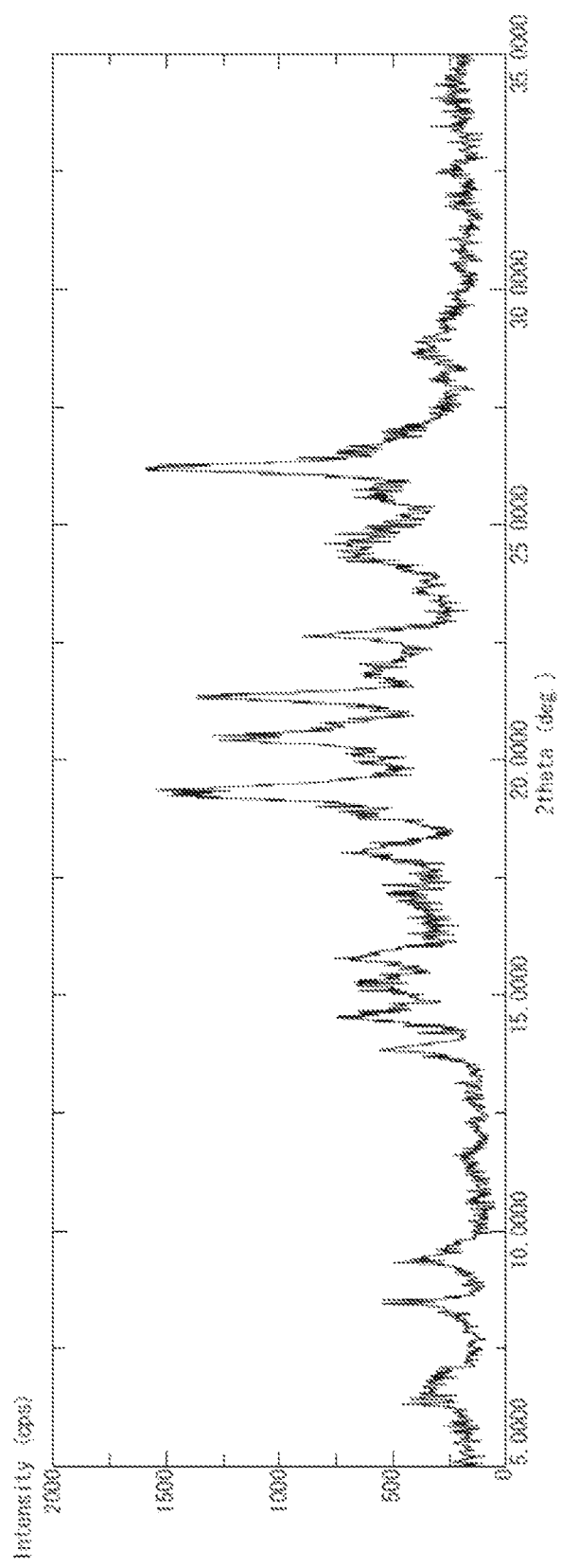
FIG. 11 is a powder X-ray diffraction pattern of the crystal of the compound (I) benzoate salt obtained in Reference Example 5. The abscissa shows the diffraction angle (2θ) and the ordinate shows the peak intensity.
Figure 12:
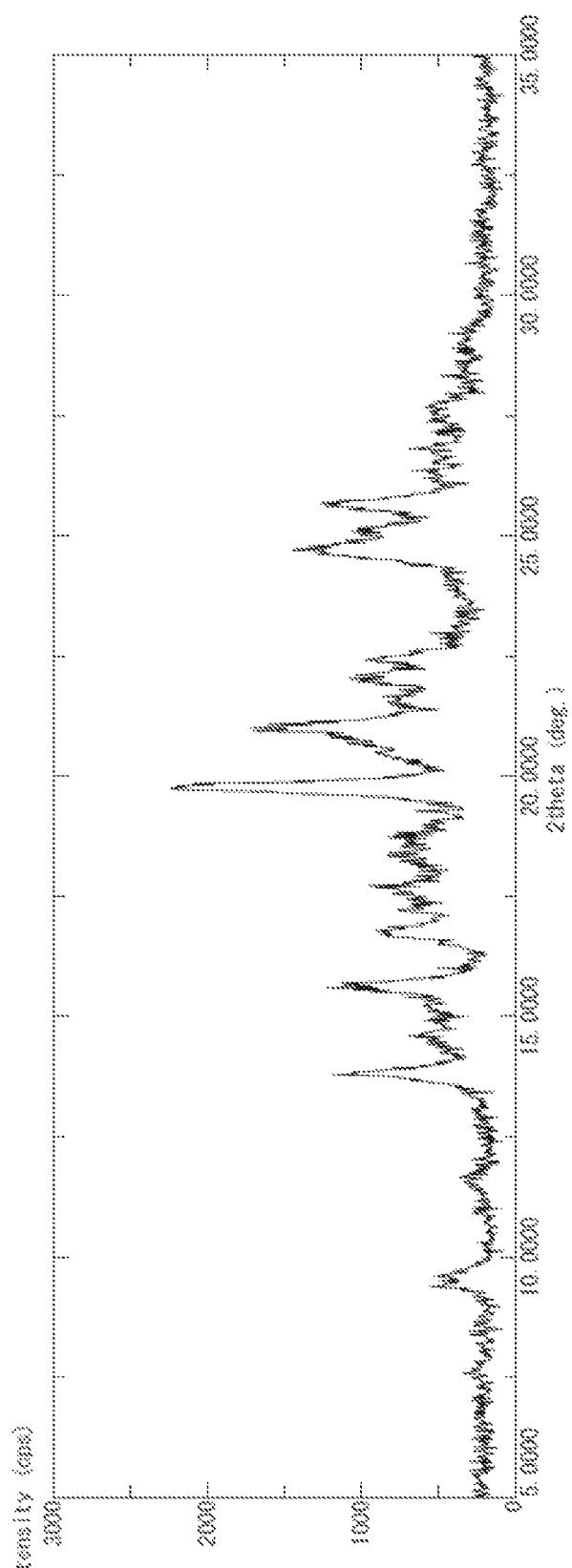
FIG. 12 is a powder X-ray diffraction pattern of the crystal of the compound (I) fumarate salt obtained in Reference Example 6. The abscissa shows the diffraction angle (2θ) and the ordinate shows the peak intensity.
Figure 13:
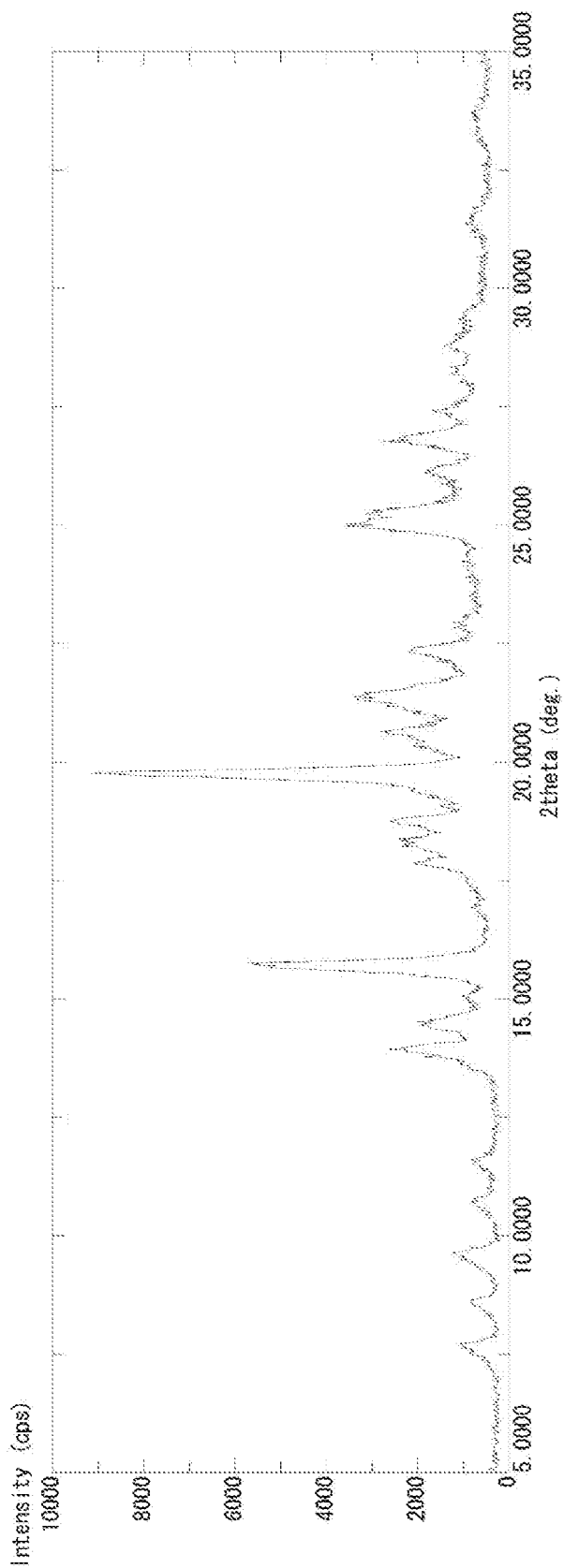
FIG. 13 is a powder X-ray diffraction pattern of the crystal of the compound (I) 0.5 succinate salt (β) obtained in Example 4. The abscissa shows the diffraction angle (2θ) and the ordinate shows the peak intensity.
Figure 14:
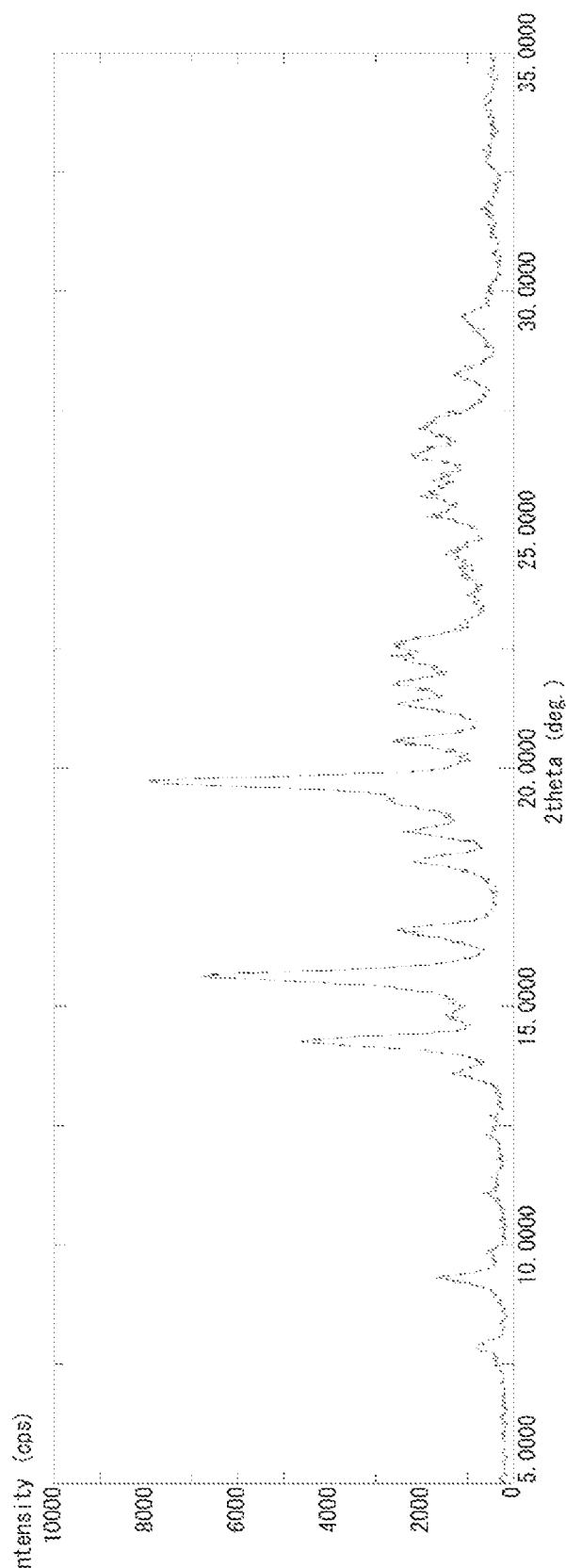
FIG. 14 is a powder X-ray diffraction pattern of the crystal of the compound (I) 0.5 succinate salt (β) obtained in Example 5. The abscissa shows the diffraction angle (2θ) and the ordinate shows the peak intensity.
Figure 15:
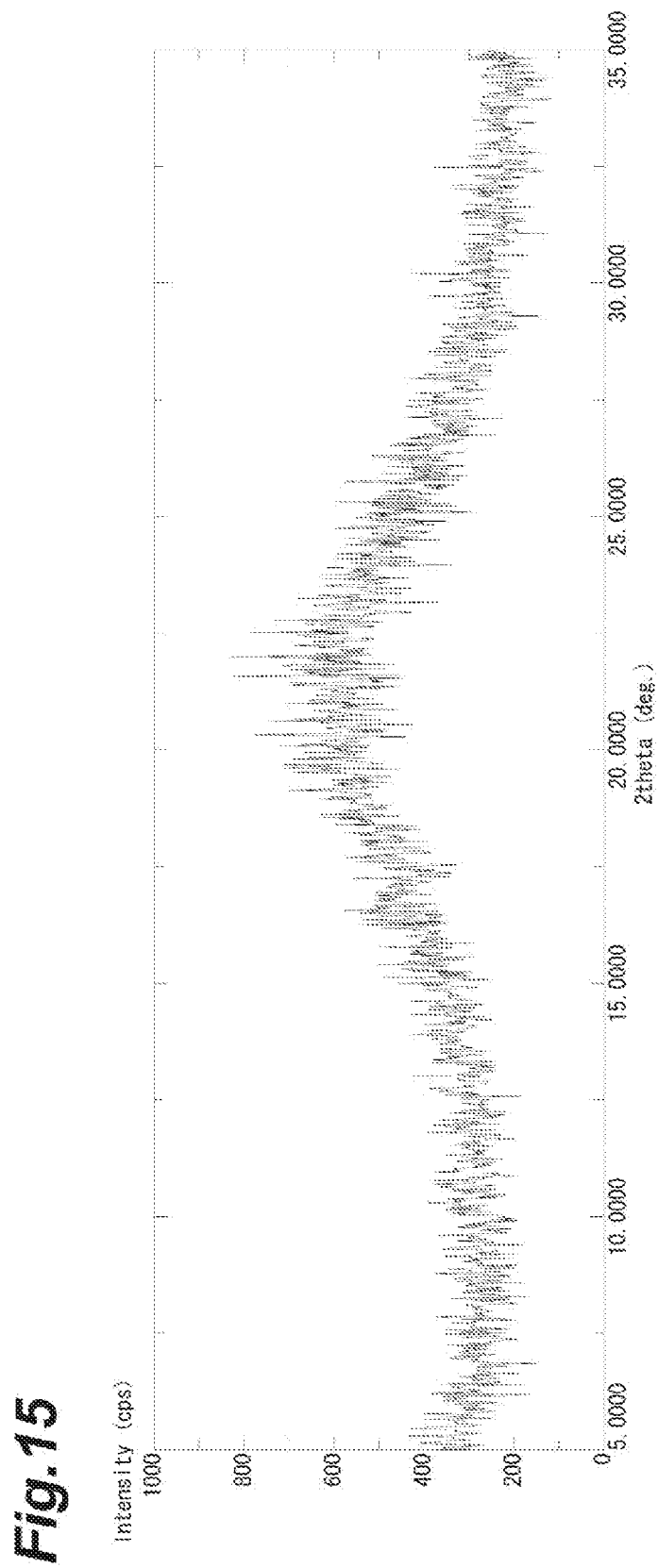
FIG. 15 is a powder X-ray diffraction pattern of the crystal of the compound (I) 1.5 succinate salt obtained in Example 6. The abscissa shows the diffraction angle (2θ) and the ordinate shows the peak intensity.

Dynamic vapour sorption apparatus was used to assess hygroscopicity of the salt of compound (I) 1.5 succinate of Example 1. The temperature of sample mounting part of the apparatus was maintained at 25° C. and relative humidity (RH) was set stepwise within a range of 5% to 95%. Relative humidity was regulated by adjusting the relative flow rates of dry 0% RH and moist 100% RH nitrogen. The weight of the sample was measured every 2 min with the micro balance. Humidity was successively changed when the width of change in weight for 5 min was less than 0.01%. The result was shown in FIG. 5.

[Test Example 2] Cell-Free Kinase Inhibitory Activity

To a flat bottom 96 well white plate (Sumitomo Bakelite Co., Ltd., MS-8496W), 10 µl of FGFR1 protein (Carna Biosciences, Inc., 08-133) solution diluted to 1 µg/mL with an assay buffer (20 mM HEPES-NaOH, 0.01% Triton X-100, 2 mM DTT, and 5 mM $MgCl_2$), 10 µL of an assay buffer solution containing CSK-tide substrate (Ana Spec Inc., 63843) in a final concentration of 1000 nM and ATP (Promega Corporation, V9102) in a final concentration of 58.3 µM, and 5 µl of a test substance diluted with the assay buffer were added, and the reaction was performed at room temperature for 1 hour. For measuring kinase activity, ADP-Glo™ Kinase Assay (Promega Corporation, V9102) was used. After the reaction, 25 µL of ADP-Glo reagent was added to each well of the plate, and the reaction was performed at room temperature for 40 minutes to stop the kinase reaction and to deplete the remaining ATP. The kinase detection reagent was further added, and the reaction was performed at room temperature for 40 minutes, so as to cause conversion from ADP to ATP, a luciferase/luciferin coupling reaction and a luminous reaction by ATP. To evaluate the enzyme activity, the amount of luminescence in each well was measured by Envision™ (PerkinElmer Co., Ltd.). The luminescence values of the wells containing the kinase protein without adding the test substance was defined as 100% and the luminescence values of the wells adding neither the test substance nor the kinase protein was defined as 0%. Then, a luminescence value ratio in the presence of the test substance was calculated. On the basis of this luminescence value ratio, the concentration of the test substance necessary for inhibiting the kinase activity by 50% (i.e., an $IC_{50}$ value) was calculated.

FGFR2 cell-free kinase inhibitory activity, FGFR3 cell-free kinase inhibitory activity, and FGFR4 cell-free kinase inhibitory activity were measured respectively by using FGFR2 protein (Carna Biosciences, Inc., 08-134), FGFR3 protein (Carna Biosciences, Inc., 08-135), or FGFR4 protein (Carna Biosciences, Inc., 08-136) in the same manner as the case of the aforementioned FGFR1 cell-free kinase inhibitory activity. However, with respect to a concentration of ATP, cell-free kinase inhibitory activity were evaluated in a final concentration of 35 µM for FGFR2, in a final concentration of 16.7 µM for FGFR3, and in a final concentration of 75 µM for FGFR4. For FGFR3 and FGFR4, the reaction with the test substance was performed at room temperature for 2 hours. Results thereof were shown in Table 1.

<Data of Cell-Free Kinase Inhibitory Activity>

TABLE 1

| Test substance | FGFR1 ($IC_{50}$ (nM)) | FGFR2 ($IC_{50}$ (nM)) | FGFR3 ($IC_{50}$ (nM)) | FGFR4 ($IC_{50}$ (nM)) |
|---|---|---|---|---|
| Compound (I) | 5.7 | 5.1 | 6.0 | 683.3 |

[Test Example 3] SNU-16 Growth Inhibition Assay

It has been reported that a human stomach cancer cell line SNU-16 (ATCC Number CRL-5974) harbors FGFR2 gene amplification (Cancer Res. 2008. 68: 2340-2348). SNU-16 cells were maintained in RPMI-1640 (Wako Pure Chemical Industries, Ltd., 187-02021) medium containing 10% FBS, and penicillin/streptomycin (Wako Pure Chemical Industries, Ltd., 168-23191) in a 5% $CO_2$ incubator (37° C.). To each well of a 96 well plate (Becton, Dickinson and Company, 35-3075), 150 µL of SNU-16 cell suspension adjusted to a concentration of $1 \times 10^4$ cells/mL with RPMI-1640 medium containing 10% FBS, and the cell was incubated overnight in a 5% $CO_2$ incubator (37° C.). On the next day, 50 µL of a test substance diluted with RPMI-1640 medium containing 10% FBS was added, and the resultant was incubated for 3 days in a 5% $CO_2$ incubator (37° C.). Then, 10 µL of Cell Counting Kit-8 (Dojindo Laboratories, CK04) was added to each well, and the resultant was incubated for 1 to 2 hours in a 5% $CO_2$ incubator (37° C.) to cause a color reaction. The absorbance value was measured with ENVISION™ (PerkinElmer Co., Ltd.) at 450 nm. Absorbance value of the wells without adding the test substance was defined as 100% and the absorbance value of the wells containing no cells was defined as 0%. Then, an absorbance ratio in the presence of the test substance was calculated. The concentration of the test substance necessary for inhibiting the cell growth by 50% (i.e., an $IC_{50}$ value) was calculated, and shown in Tables 2.

<Data of Evaluation of SNU-16 Growth Inhibitory Activity>

TABLE 2

| Test substance | SNU-16 ($IC_{50}$ (nM)) |
|---|---|
| Compound (I) | 4.2 |

[Test Example 4] Antitumor Effect in SNU-16 Subcutaneous Xenograft Model in Mice Human stomach cancer cell line SNU-16, which had been cultured in an RPMI-1640 medium containing 10% FBS, and penicillin/streptomycin, were adjusted to a concentration of $1 \times 10^8$ cells/mL with Hanks' Balanced Salt Solution (GIBCO #24020) to prepare a cell suspension, and the suspension was mixed with MATRIGEL (BD Biosciences, Cat#354234) in a ratio of 1:1 to prepare a cell suspension in a concentration of $5 \times 10^7$ cells/mil. The cell suspension was inoculated in a volume of 100 µL into a subcutaneous part of a right flank of nude mice, 6 to 7 weeks of ages (BALB/cAJcl-nu/nu, female, Clea Japan Inc.). Seven days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formula:

Tumor volume (mm³)=Longest diameter (mm)×
Shortest diameter (mm)×Shortest diameter (mm)/2

On the basis of the volumes of tumors obtained on the first day of administration, the nude mice were grouped such that averages of the tumor volumes were substantially equal among the groups. Each test substance was dissolved in DMSO, Tween 80 was added thereto to prepare a solution in a 10-fold concentration and the thus prepared solution was stored at the freezer before use. Immediately before the administration, the stock solution was diluted with a 5% glucose solution to obtain a final administration solution (in which a ratio in % among DMSO, Tween 80 and the 5% glucose solution was 3.5:6.5:90). Each evaluation sample was orally administered to test substance administration group at a volume of 20 mL/Kg once a day continuously for 11 days, and in a control group, an administration solvent was orally administered under the same conditions. Incidentally, the experiment was conducted on groups each consisting of 5 mice.

With respect to each of the control group and test substance administration group, a ratio of the weight measured on the final day to the weight measured on the first day (relative body weight: RBW) was calculated. If a ratio of the RBW of the test substance administration group/the RBW of the control group is 0.9 or more, the corresponding test substance administration group was defined as a well-tolerated. In the test substance administration group thus defined as well-tolerated, a ratio of the tumor volume of the test substance-dosing group to the tumor volume of the control group obtained on the last day (T/C) (%) was calculated, and shown in Table 3.

<Data of Evaluation of Antitumor Effect in SNU-16 Subcutaneous Xenograft Model in Mice>

TABLE 3

| Test substance | Dosage (mg/kg) | T/C (%) |
|---|---|---|
| Compound (I) | 6.25 | 49 |
|  | 12.5 | 26 |
|  | 25 | 16 |
|  | 50 | 7 |

What is claimed is:

1. A salt consisting of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide represented by formula (I):

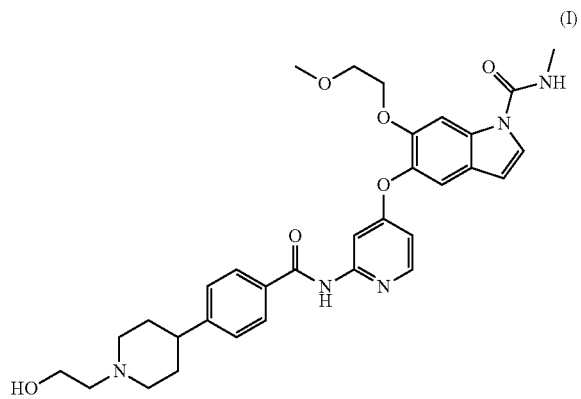 [SMILES: CNC(=O)n1ccc2cc(Oc3ccnc(NC(=O)c4ccc(C5CCN(CCO)CC5)cc4)c3)c(OCCOC)cc21]

and succinic acid or maleic acid.

2. The salt according to claim 1, which is a succinate salt.
3. The salt according to claim 2, which is 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 1.5 succinate salt.
4. The salt according to claim 2, which is 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 0.5 succinate salt.
5. The salt according to claim 1, which is 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide maleate salt.
6. A crystal of a salt consisting of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide represented by formula (I):

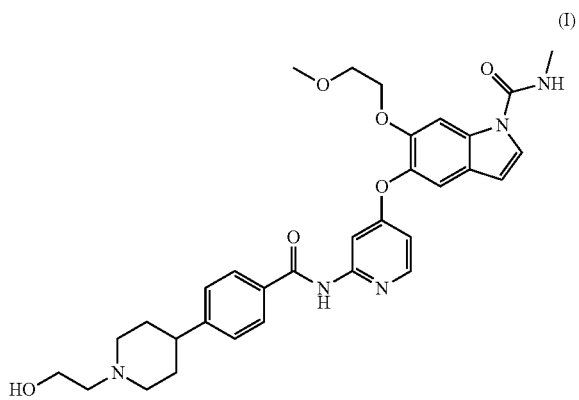 [SMILES: CNC(=O)n1ccc2cc(Oc3ccnc(NC(=O)c4ccc(C5CCN(CCO)CC5)cc4)c3)c(OCCOC)cc21]

and succinic acid.

7. A crystal of a salt consisting of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide represented by formula (I):

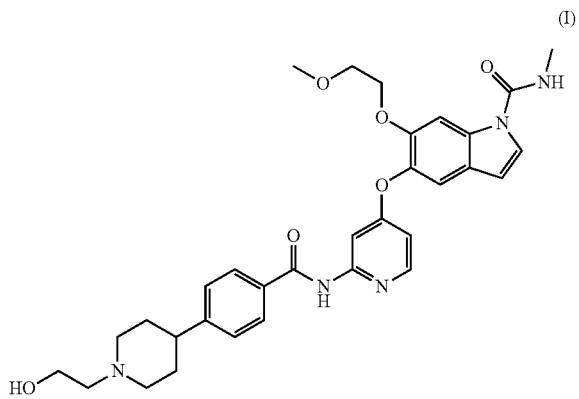 [SMILES: CNC(=O)n1ccc2cc(Oc3ccnc(NC(=O)c4ccc(C5CCN(CCO)CC5)cc4)c3)c(OCCOC)cc21]

and maleic acid.

8. A crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 1.5 succinate salt, having a diffraction peak at a diffraction angle (2θ±0.2°) of 22.4° in a powder X-ray diffraction.
9. The crystal according to claim 8, having diffraction peaks at diffraction angles (2θ±0.2°) of 22.4°, 25.3° and 23.3° in a powder X-ray diffraction.

10. A crystal (α) of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 0.5 succinate salt, having a diffraction peak at diffraction angles (2θ±0.2°) of 19.8° in a powder X-ray diffraction.

11. A crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide maleate salt, having a diffraction peak at a diffraction angle (2θ±0.2°) of 20.1° in a powder X-ray diffraction.

12. A crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 1.5 succinate salt, having peaks at chemical shifts (±0.5 ppm) of 108.5 ppm, 155.1 ppm and 179.9 ppm in a $^{13}$C solid state NMR spectrum.

13. The crystal according to claim 12, having peaks at chemical shifts (±0.5 ppm) of 27.1 ppm, 34.8 ppm, 108.5 ppm, 155.1 ppm and 179.9 ppm in a $^{13}$C solid state NMR spectrum.

14. A crystal of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide 1.5 succinate salt, having a powder X-ray diffraction pattern as shown in FIG. 1.

15. A pharmaceutical composition comprising the salt according to claim 1 as an active ingredient.

16. A pharmaceutical composition comprising the crystal according to claim 6 as an active ingredient.

17. A pharmaceutical composition comprising the crystal according to claim 8 as an active ingredient.

18. A pharmaceutical composition comprising the crystal according to claim 12 as an active ingredient.

19. A pharmaceutical composition comprising the crystal according to claim 14 as an active ingredient.

* * * * *